US010371671B2

(12) United States Patent
Ortmann et al.

(10) Patent No.: US 10,371,671 B2
(45) Date of Patent: Aug. 6, 2019

(54) BRANCHING OFF FLUIDIC SAMPLE WITH LOW INFLUENCE ON SOURCE FLOW PATH

(71) Applicant: Agilent Technologies, Inc., Santa Clara, CA (US)

(72) Inventors: Thomas Ortmann, Straubenhardt/Ottenhausen (DE); Daniel Thielsch, Straubenhardt/Ottenhausen (DE)

(73) Assignee: Agilent Technologies, Inc., Santa Clara, CA (US)

( * ) Notice: Subject to any disclaimer, the term of this patent is extended or adjusted under 35 U.S.C. 154(b) by 216 days.

(21) Appl. No.: 15/608,888

(22) Filed: May 30, 2017

(65) Prior Publication Data

US 2017/0343520 A1    Nov. 30, 2017

(30) Foreign Application Priority Data

May 30, 2016    (DE) .......................... 10 2016 109 914

(51) Int. Cl.
| | | |
|---|---|---|
| *G01N 30/20* | (2006.01) | |
| *G01N 30/04* | (2006.01) | |
| *G01N 30/10* | (2006.01) | |
| *G01N 30/36* | (2006.01) | |
| *B01D 15/14* | (2006.01) | |
| *G01N 30/32* | (2006.01) | |

(52) U.S. Cl.
CPC ............ *G01N 30/20* (2013.01); *B01D 15/14* (2013.01); *G01N 30/04* (2013.01); *G01N 30/10* (2013.01);
(Continued)

(58) Field of Classification Search
CPC ....... G01N 2030/202; G01N 2030/207; G01N 2030/382; G01N 30/04; G01N 30/28;
(Continued)

(56) References Cited

U.S. PATENT DOCUMENTS 4,470,316 A * 9/1984 Jiskoot ................. G01N 1/2042
                                                            222/249
4,722,830 A    2/1988 Urie et al.
(Continued)

FOREIGN PATENT DOCUMENTS

DE    102014101617 A1    4/2014
DE    102014110544 B3    9/2015
(Continued)

OTHER PUBLICATIONS

European Extended Search Report dated Aug. 16, 2017 from related European Application No. 17172861.1.

*Primary Examiner* — Nathaniel J Kolb

(57) ABSTRACT

A sample management device which comprises a source flow path in which a fluidic sample can flow, a volume flow adjustment unit configured to adjust a volume flow of the fluidic sample to be branched off from the source flow path at a fluidic coupling point, and a fluidic valve fluidically coupled with the source flow path and with the volume flow adjustment unit, wherein the fluidic valve is switchable into a branch off state in which the fluidic coupling point is established within the source flow path to branch off an adjustable volume of the fluidic sample from the source flow path via the fluidic coupling point while a flow of the fluidic sample in the source flow path continues.

17 Claims, 11 Drawing Sheets

(52) U.S. Cl.
CPC ....... *G01N 30/36* (2013.01); *G01N 2030/201* (2013.01); *G01N 2030/202* (2013.01); *G01N 2030/207* (2013.01); *G01N 2030/324* (2013.01); *G01N 2030/326* (2013.01); *G01N 2030/328* (2013.01)

(58) Field of Classification Search
CPC ...... G01N 30/36; G01N 30/38; G01N 1/2035; G01N 1/2042; G01N 2001/205; G01N 2001/2064
See application file for complete search history.

(56) References Cited

U.S. PATENT DOCUMENTS

| | | | | |
|---|---|---|---|---|
| 5,736,654 | A * | 4/1998 | Dubois | ................ G01N 1/2042 73/863.84 |
| 5,746,153 | A | 5/1998 | Hoefelmayr | |
| 7,575,723 | B2 | 8/2009 | Nichols et al. | |
| 9,133,833 | B2 | 9/2015 | Picha et al. | |
| 2005/0223996 | A1* | 10/2005 | Bosma | ...................... A01J 5/01 119/14.02 |
| 2011/0045599 | A1* | 2/2011 | Erickson | ........... B01L 3/502738 436/110 |
| 2012/0305464 | A1* | 12/2012 | Cormier | ................. G01N 30/20 210/198.2 |
| 2016/0025762 | A1* | 1/2016 | Vautz | ................... G01N 1/2247 73/864.81 |

FOREIGN PATENT DOCUMENTS

| | | |
|---|---|---|
| EP | 1577012 A1 | 3/1926 |
| GB | 2345118 A | 6/2000 |
| WO | 2010139359 A1 | 12/2010 |
| WO | 2011106162 A1 | 9/2011 |
| WO | 2016075503 A1 | 5/2016 |

* cited by examiner

BRANCHING OFF FLUIDIC SAMPLE WITH LOW INFLUENCE ON SOURCE FLOW PATH

RELATED APPLICATIONS

This application claims priority under 35 U.S.C. § 119(a) to German Patent Application No. DE 10 2016 109 914.7, filed May 30, 2016, the content of which is incorporated herein by reference in its entirety.

BACKGROUND ART

The present invention relates to a sample management device, a method of managing a fluidic sample, and a sample separation system.

In liquid chromatography, a fluidic sample and an eluent (liquid mobile phase) may be pumped through conduits and a separation unit such as a column in which separation of sample components takes place. The column may comprise a material which is capable of separating different components of the fluidic sample. The separation unit may be connected to other fluidic members (like a sampler or an injector, a detector) by conduits. Before the fluidic sample is introduced into a separation path between a fluid drive unit (in particular a high pressure pump) and the separation unit, a predefined amount of fluidic sample shall be intaken from a sample source (such as a sample container) via an injection needle into a sample loop by a corresponding movement of a piston within a metering device. This usually occurs in the presence of a significantly smaller pressure than what the separation unit is run with. Thereafter, an injector valve is switched so as to introduce the intaken amount of fluidic sample from the sample loop of a metering path into the separation path between fluid drive unit and the separation unit for subsequent separation.

Injector valves may be configured as rotatable valves having a stator (which may have one or a plurality of fluid ports) and a rotor (which may have a plurality of grooves for connecting respective ones of the fluid ports) being rotatable with regard to the stator to thereby establish a desired fluid communication state between fluid ports and grooves. In order to be capable to withstand high pressure values of for instance up to 1200 bar in a fluid tight manner, it is necessary to press the rotor against the stator.

U.S. Pat. No. 7,575,723 discloses that, while a large primary stream of analytes flows from a chromatographic column to containers of a receiver, small samples of the analytes are diverted for flow to a mass spectrometer for analysis, by use of a transfer module. The transfer module includes a stator and a rotor or shuttle. The shuttle has an aliquot passage that initially lies in a first position where the primary stream flows through it so the aliquot passage receives a small sample. The shuttle then moves to a second position where the aliquot passage is aligned with a pump that pumps fluid out of the aliquot passage to the mass spectrometer.

U.S. Pat. No. 9,133,833 discloses methods and an apparatus for moving aliquot samples of fluid using a shuttle valve.

GB 2,345,118 discloses an injection valve which comprises a plurality of ports connected in pairs to allow fluid to flow in through a respective port and out through a second respective port and is characterised by an additional port provided in the fluid flow path of two connected ports, to provide a third port in that path. An analytical apparatus uses the valve to obtain varying concentrations of standard solution in an automated process for calibrating the apparatus.

U.S. Pat. No. 4,722,830 discloses an automated analysis system which includes a pair of sample selection subsystems whose operations are coordinated by a host computer pursuant to developing analytical data useful to a process computer in controlling an industrial process. Each subsystem includes a sample selection computer operating to control one or more multiport valves in extracting fluid samples on a scheduled or demand basis from sample loops connected with the various process streams involved with the process. The extracted samples are injected into a spectrometer for analysis. An instrument computer converts the spectrometer responses to analytical data indicative of the constituent concentrations found in an analyzed sample.

However, the functionality of conventional sample management systems is limited.

DISCLOSURE

It is an object of the invention to provide a flexibly operable sample management system.

According to an exemplary embodiment of the present invention, a sample management device is provided which comprises a source flow path in which a fluidic sample can flow, a volume flow adjustment unit configured for adjusting a volume flow of the fluidic sample to be branched off from the source flow path at a fluidic coupling point, and a fluidic valve fluidically coupled with the source flow path and with the volume flow adjustment unit, wherein the fluidic valve is switchable into a branch off state in which the fluidic coupling point is established within (in particular by a switching procedure of switching the fluidic valve) or is coupled into the source flow path to branch off an adjustable volume of the fluidic sample from the source flow path via the fluidic coupling point while a flow of the fluidic sample in the source flow path continues.

According to another exemplary embodiment, a method of managing a fluidic sample is provided, wherein the method comprises providing a fluidic sample flowing in a source flow path, fluidically coupling a fluidic valve with the source flow path and with a volume flow adjustment unit configured for adjusting a volume flow of the fluidic sample to be branched off from the source flow path at a fluidic coupling point, and switching the fluidic valve into a branch off state in which the fluidic coupling point is established within (or coupled into) the source flow path (in particular by the switching), and branching off a volume, being adjusted by the volume flow adjustment unit, of the fluidic sample from the source flow path via the fluidic coupling point while a flow of the fluidic sample in the source flow path continues and while the fluidic valve is in the branch off state.

According to still another exemplary embodiment, a sample separation system for separating a fluidic sample is provided, wherein the sample separation system comprises a fluid drive configured for driving a mobile phase, a separation unit configured for separating the fluidic sample in the mobile phase, and a sample management device having the above mentioned features for branching off an adjusted volume the fluidic sample for injection between the fluid drive and the separation unit.

According to an exemplary embodiment of the invention, a sample management system is provided which allows to branch off a defined amount of a fluidic sample from a source flow path without disturbing flow of the fluidic sample in this source flow path. This can be accomplished by a fluidic valve which is capable of establishing, generating or switching a fluidic coupling point (such as a fluidic T-point) into the source flow path so as to temporarily initiate a flow of a specific amount of the fluidic sample from the source flow path via the fluidic coupling point into a fluid accommodation volume in fluid communication with a volume flow adjustment unit. The volume flow adjustment unit may have the capability of precisely adjusting a volume of the fluidic sample to be branched off. Such an adjustment may be accomplished in such a way that the conditions in the source flow path remain substantially undisturbed, so that any process in the source flow path by which the fluidic sample is processed may continue regardless of the branching off of a specific portion of the fluidic sample. This allows for simultaneously monitoring an ongoing sample processing in the source flow path. By the concept of the temporarily establishing the fluidic coupling point within the source flow path, a remaining very small influence on the source flow path may be limited not only in terms of intensity but also in terms of time. Thus, a certain amount of fluidic sample which can be precisely controlled and defined by the volume flow adjustment unit can be branched off from the substantially undisturbed source flow path. Advantageously, an only temporary switching of the fluidic coupling point for establishing a fluidic connection between the source flow path and the volume flow adjustment unit keeps the dead volume in the fluidic system very small, thereby reducing issues in terms of undesired carry-over of fluidic sample, etc.

In the following, further embodiments of the sample management device, the sample separation system, and the method will be explained.

In an embodiment, the temporarily established fluidic connection point or flow coupler is configured as a fluidic T-piece, a fluidic Y-piece, or a fluidic X-piece, In case of a fluidic T-piece and a fluidic Y-piece, two flow streams are combined at one bifurcation point into a single outlet path. In the case of a fluidic X-piece, there may be one further fluid conduit. This further fluid conduit can be a second fluid outlet conduit or a third fluid inlet conduit. Other kinds of flow couplers are possible as well.

In an embodiment, the fluidic valve is configured so that a flow of the fluidic sample in the source flow path continues substantially undisturbed in the branch off state. The term "substantially undisturbed in the branch off state" may particularly denote that a flow rate, a pressure, a fluid processing, etc. may remain substantially constant during branching off.

In particular, the fluidic valve may be configured so that a flow of the fluidic sample in the source flow path continues uninterruptedly in the branch off state. In the context of the present application, the term "flow of the fluidic sample in the source flow path continues uninterruptedly in the branch off state" may particularly denote that artefacts in a pressure curve concerning the fluidic sample in the source flow path can be suppressed or even eliminated, since the flow of the fluidic sample is never reduced to zero regardless of branching off fluidic sample.

This can be accomplished by keeping the pressure conditions in a fluidic path connected to the volume flow adjustment unit on the one hand and in the source flow path on the other hand as similar as possible so as to avoid pressure peaks or switching artefacts or even an undesired pressure reduction or increase upon switching the volume flow adjustment unit into fluid communication with the source flow path. At the fluidic coupling point, which may be a fluidic T-point within the fluidic valve, a portion of the fluidic sample may continue to flow through the source flow path while another portion may be split towards the volume flow adjustment unit as a consequence of the establishing of the fluidic coupling point within the source flow path and within the fluidic valve.

In an embodiment, the fluidic coupling point is located in an interior of the fluidic valve. By integrating the fluidic coupling point in the fluidic valve, the length of the fluidic conduit from the source flow path towards the fluidic path extending from the fluidic coupling point to the volume flow adjustment unit may be kept very small. Consequently, also the dead volume may be kept very small. This reduces issues concerning carry-over of sample and keeps losses of fluidic sample small. When located in an interior of the fluidic valve, the fluidic coupling point may also be selectively switched out of fluid communication with the source flow path, thereby keeping the source flow path as uninfluenced as possible regardless of the branching off.

In an embodiment, the fluidic valve is configured so that the volume flow adjustment unit is fluidically coupled with the source flow path via the fluidic coupling point having at least three, in particular exactly three, fluid connections defined at least partially by the fluidic valve in the branch off state. When being configured with exactly three fluidic connections, the fluidic coupling point may define a fluidic T-point. However, it is also possible that the fluidic coupling point defines a fluidic Y-connection, or even a fluidic X-connection with four fluidic connections. The number of fluidic connections can be selected in accordance with the requirements of a certain application.

In an embodiment, two of the at least three fluid connections at the fluidic coupling point are fluidically coupled to or form part of the source flow path and another one of the at least three fluid connections is fluidically coupled to the volume flow adjustment unit. One of the fluid connections forming part of the source flow path may correspond to a fluidic conduit via which the fluidic sample flows towards the fluidic coupling point. The second fluid connection relating to the source flow path may correspond to a fluidic conduit through which the fluidic sample flows away from the fluidic coupling point. The fluidic coupling point relating to the fluidic valve may correspond to a fluid connection which directs the branched off fluidic sample towards a sample accommodation volume operated by the volume flow adjustment unit.

In an embodiment, the at least three fluid connections comprise two fluidic conduits of the fluidic valve fluidically coupled with one another in the branch off state (in particular one fluidic conduit of a stator and one fluidic conduit of a rotor) of the fluidic valve. For example, at least part of the fluidic conduits may be provided as grooves of a rotor and a stator of the fluidic valve. Generally, a stator of a fluidic valve may comprise one or more ports at which fluid connections to connected fluidic members may be accomplished. Furthermore, a rotor of a fluidic valve may comprise one or more fluidic conduits, such as grooves, selectively coupling or decoupling individual ones of the ports in different switching states of the fluidic valve. However, it is alternatively also possible that also the stator comprises one or more fluid conduits such as grooves to extend the functionality of the fluidic valve in terms of adjustable fluidic connections and fluidic decoupling configurations. By providing fluidic conduits such as grooves in both stator and rotor, the length of the flow paths may be kept small, which is advantageously in terms of small dead volume and other effects.

In an embodiment, the fluidic coupling point corresponds to a fluid port, in particular a fluid port of a stator, of the fluidic valve. Such a port is a spatially strictly limited fluidic coupling point keeping the dead volume small.

In an embodiment, the volume flow adjustment unit comprises an adjustment pump, in particular a metering pump. In particular, the volume flow adjustment unit may comprise a piston which can be configured for moving selectively forwardly or backwardly within a piston chamber. By such a forward or backward motion, in particular in conjunction with a corresponding pressure provided by the piston, the pressure conditions between volume flow adjustment unit and source flow path may be precisely controlled. Therefore, the configuration of the volume flow adjustment unit as such a piston driven pump is highly advantageously.

In an embodiment, the adjustment pump is configured for adjusting the volume of the fluidic sample to be branched off from the source flow path. Control of the pumping characteristics can be accomplished by controlling the time over position trajectory of the piston. For branching off, a controlled amount (such as a controlled volume or—for a temperature independent or pressure independent operation—a controlled amount of molecules) of fluidic sample can be branched off at the fluidic coupling point.

Prior to connecting the adjustment pump with the source flow path, it is possible that the pressure in a sample accommodation volume (which may be a sample loop) in fluid connection with the adjustment pump is brought to (or close to) a pressure of the source flow path (such as a reactor). After branching off fluidic sample from the source flow path into the sample accommodation volume, it is possible that the adjustment pump carries out a pressure adjustment (for instance by a piston of the adjustment pump driving in a backward direction for accomplishing a pressure release of the fluid). In a further embodiment, a negative pressure operation of a reactor can be carried out, i.e. accomplishing pressure reduction for switching the sample accommodation volume in fluid connection with the source flow path, and pressure increase (for instance ambient pressure) for fluidically decoupling the sample accommodation volume from the source flow path. However, it should be said that the description herein is independent of absolute pressure (for instance in a pressure range between 0 and 2000 bar).

In an embodiment, the volume flow adjustment unit comprises or consists of a predefined fluidic restriction. Such a predefined fluidic restriction may be a barrier for the fluidic sample flowing from the fluidic coupling point towards the fluidic restriction. Therefore, such a fluidic restriction limits the amount of fluidic sample split or branched off towards the volume flow adjustment unit. Thus, a completely passive and hence very simple configuration of the volume flow adjustment unit is possible in which the volume flow is adjusted by the value of a fluidic resistance.

In an embodiment, the volume of the fluidic sample to be branched off from the source flow path flows into a sample accommodation volume, in particular a sample loop. Such a sample accommodation volume may be a defined storage volume for the branched off fluidic sample to assume before the branched off fluidic sample is transported to a destination for further fluid processing.

In an embodiment, the sample management device comprises a destination flow path fluidically coupled with the fluidic valve being switchable into a sample supply state in which the branched off fluidic sample is supplied into the destination flow path. Thus, by a further switching of the fluidic valve into the sample supply state, the previously branched off fluidic sample can be transported to a destination flow path for further fluid processing. Advantageously, introducing the branched off amount of fluidic sample into the destination flow path may also be carried without disturbing or interrupting fluid processing in the destination flow path.

In an embodiment, the source flow path is configured for closed-loop fluid processing. Thus, the fluidic sample may be continuously processed in the source flow path, for instance driven by a pump.

In an embodiment, the source flow path comprises a fluid reactor for subjecting the fluidic sample to a reaction. When a fluid reactor is implemented in or as the source flow path, the result of the reaction of the fluidic sample in the reactor may be branched off by the volume flow adjustment unit for further processing. Thus, a reaction can be monitored quasi continuously without disturbing the reaction in the source flow path.

In an embodiment, the source flow path comprises a sample separation apparatus for separating the fluidic sample in fractions (for instance by liquid chromatography). Therefore, the fluidic sample separated into fractions in the source flow path may be branched off, for instance fractionwise, by the volume flow adjustment unit. For instance, the volume flow adjustment unit may form part of a fractioner.

In an embodiment, the destination flow path comprises a further sample separation apparatus for further separating the fractions in sub-fractions. In this configuration, it is in particular possible that the system of source flow path, fluidic valve and destination flow path form a two-dimensional sample separation apparatus or system, in particular a two-dimensional liquid chromatography sample separation apparatus or system (2DLC). A flow from the first dimension into the second dimension may be transferred substantially without influencing the fluid separation in the first dimension. In such an embodiment, a fluidic sample (for instance including one fraction) is taken out of the first dimension and is supplied to the second dimension. The separation in the first dimension keeps uninfluenced from the branching off, since the fluidic sample may be branched off from the source flow path only downstream of a separation unit and without flow interruption.

In an embodiment, the sample management device comprises a needle, a seat and an accommodation volume between the volume flow adjustment unit and the fluidic valve, wherein the needle is drivable selectively into the seat or out of the seat for transferring a substance between the accommodation volume and an external entity, in particular a fluid container. Thus, the portion of the sample supply device between the fluidic coupling point and the volume flow adjustment unit, including needle, seat and accommodation volume, may be configured as an injector. The needle may drive out of the seat for injecting fluidic sample which has been previously branched off from a source flow path into a separate apparatus, for instance a separate liquid chromatography apparatus. But it is also possible that the needle drives into a fluid container such as a vial before intaking a medium.

In an embodiment, the sample management device comprises a sample separation apparatus into which the branched off fluidic sample is injectable from the external entity (such as a vial or fluid container). Such an embodiment is shown in FIG. 7 to FIG. 11.

In an embodiment, the sample separation apparatus comprises a further needle, a further seat and a further accommodation volume, wherein the further needle is drivable selectively into the further seat or out of the further seat for transferring the branched off fluidic sample from the external entity into the further accommodation volume. It is alternatively also possible that a common needle is used for the injector portion of the sample management device and the further injector portion of the sample management device. By taking this measure, a vial for temporarily storing the branched off fluidic sample may be dispensable.

In an embodiment, the fluidic valve is switchable in a pressure adjustment state in which the source flow path is fluidically decoupled from the volume flow adjustment unit and in which the volume flow adjustment unit is operable for adjusting a pressure within a path which extends between the volume flow adjustment unit and the fluidic valve. Thereby, the pressure in the volume flow adjustment unit and the pressure in the source flow path may be mutually adjusted. In particular, the volume flow adjustment unit may be operable for adjusting the pressure in the pressure adjustment state to reduce a pressure difference to another pressure in the source flow path prior to switching the fluidic valve in the branch off state. Thus, pre-compression or decompression is possible while the sample management device is in the pressure adjustment state. Thereby, differing pressures in the source flow path and the fluidic path connected to the volume flow adjustment unit can be adjusted to one another prior to coupling them in the branch off state, thereby preventing pressure shocks and other artefacts.

In an embodiment, the fluidic valve comprises a stator and a rotor being rotatable relative to one another, wherein the stator comprises a plurality of ports and optionally one or more fluid conduits, and the rotor comprises at least one fluid conduit (in particular a plurality of fluid conduits, such as one or more grooves). The conduit(s) may be selectively fluidically coupled with or decoupled from the stator ports by rotating the rotor relative to the stator.

In an embodiment, the fluidic valve has at least the following ports (which may be established as part of a stator of a rotatable fluidic valve):
- a source flow-in port through which the fluidic sample can be guided to flow from the source flow path into the fluidic valve;
- a source flow-out port (which may be equal to the fluidic coupling point, for instance in the branch off state) through which branched off fluidic sample can flow away from the source flow path and not-branched off fluidic sample can remain flowing within the source flow path; and
- a branch off port (which may be a central port of the fluidic valve) through which the branched off fluidic sample can flow to a sample accommodation volume in fluid communication with the volume flow adjustment unit.

By such a valve configuration, branching off a portion of the fluidic sample may be accomplished with very low impact on the source flow path and with small dead volume.

Correspondingly, the fluidic valve may have an "in" and an "out" connection for the source flow path as well as a channel end point, which may be fluidically coupled to the volume flow adjustment unit, for providing or establishing the fluidic coupling point (in particular in a dedicated switching state of the fluidic valve such as the branch off state).

In an embodiment, the fluidic valve is switchable into at least one other state (i.e. in a switching state which differs from the branch off state) in which no fluidic coupling point (of the above described type) fluidically coupling the volume flow adjustment unit and the source flow path is established within the source flow path. Thus, the fluidic coupling point may be a temporary fluidic coupling point (such as a temporary fluidic T-junction) which is established only in a specific switching state of the fluidic valve, but is absent in another switching state of the fluidic valve.

In an embodiment, the fluidic coupling point is defined by a fluidic coupling position between the source flow path and a channel end point (see reference numeral 145 in FIG. 3) of a volume flow adjustment path including the volume flow adjustment unit. The channel end point may be constituted as the dead end of a rotor groove of the fluidic valve fluidically coupled with the volume flow adjustment unit. This enables a temporary formation of a fluidic T-point or the like for sample branch off with small or even zero dead volume (so that undesired sample carryover as well as non-flushed channels can be prevented).

In an embodiment, the fluidic valve is switchable into at least one other state (i.e. another state than the branch off state) in which the volume flow adjustment unit and the source flow path are decoupled from one another. Thus, the fluidic connection between source flow path and a sample accommodation volume operated by the volume flow adjustment unit can be established only temporarily in a certain valve position (i.e. in the branch off state, compare for instance FIG. 2), whereas in one or more other valve positions (such as in the sample supply state, compare for instance FIG. 4), such a fluidic T-piece (or the like) establishing a fluidic coupling of source flow path and sample accommodation volume via the fluidic coupling point is removed or inactive. This allows to keep the dead volume very small and also allows for a pressure equilibration. In one embodiment, the fluidic valve may be switchable into at least one state in which the fluidic coupling point is decoupled from source flow path and/or volume flow adjustment unit or is absent at all.

Embodiments of the above described sample management device may be implemented in or functionally connected to conventionally available HPLC systems, such as the Agilent 1200 Series Rapid Resolution LC system or the Agilent 1100 HPLC series (both provided by the applicant Agilent Technologies—see www.agilent.com—which shall be incorporated herein by reference).

One embodiment of a sample separation apparatus or system, in which a sample management device of the above described type may be implemented, comprises a pumping apparatus as fluid drive or mobile phase drive having a pump piston for reciprocation in a pump working chamber to compress liquid in the pump working chamber to a high pressure at which compressibility of the liquid becomes noticeable.

The separation unit of the sample separation system preferably comprises a chromatographic column (see for instance en.wikipedia.org/wiki/Column_chromatography) providing the stationary phase. The column may be a glass or steel tube (for instance with a diameter from 50 μm to 5 mm and a length of 1 cm to 1 m) or a microfluidic column (as disclosed for instance in EP 1577012 or the Agilent 1200 Series HPLC-Chip/MS System provided by the applicant Agilent Technologies). The individual components are retained by the stationary phase differently and at least partly separate from each other while they are propagating at different speeds through the column with the eluent. At the end of the column they elute one at a time or at least not entirely simultaneously. During the entire chromatography process the eluent may be also collected in a series of fractions. The stationary phase or adsorbent in column chromatography usually is a solid material. The most common stationary phase for column chromatography is silica gel, surface modified silica gel, followed by alumina. Cellulose powder has often been used in the past. Also possible are ion exchange chromatography, reversed-phase chromatography (RP), affinity chromatography or expanded bed adsorption (EBA). The stationary phases are usually finely ground powders or gels and/or are microporous for an increased surface.

The mobile phase (or eluent) can be a pure solvent or a mixture of different solvents (such as water and an organic solvent such as ACN, acetonitrile). It can be chosen for instance to minimize the retention of the compounds of interest and/or the amount of mobile phase to run the chromatography. The mobile phase can also be chosen so that the different compounds or fractions of the fluidic sample can be separated effectively. The mobile phase may comprise an organic solvent like for instance methanol or acetonitrile, often diluted with water. For gradient operation water and organic is delivered in separate bottles, from which the gradient pump delivers a programmed blend to the system. Other commonly used solvents may be isopropanol, tetrahydrofuran (THF), hexane, ethanol and/or any combination thereof or any combination of these with aforementioned solvents.

The fluidic sample may comprise but is not limited to any type of process liquid, natural sample like juice, body fluids like plasma or it may be the result of a reaction like from a fermentation broth.

The pressure, as generated by the fluid drive, in the mobile phase may range from 2-200 MPa (20 to 2000 bar), in particular 10-150 MPa (100 to 1500 bar), and more particularly 50-120 MPa (500 to 1200 bar).

The sample separation apparatus or system, for instance an HPLC system, may further comprise a detector for detecting separated compounds of the fluidic sample, a fractionating unit for outputting separated compounds of the fluidic sample, or any combination thereof. Further details of such an HPLC system are disclosed with respect to the Agilent 1200 Series Rapid Resolution LC system or the Agilent 1100 HPLC series, both provided by the applicant Agilent Technologies, under www.agilent.com which shall be in cooperated herein by reference.

Embodiments of the invention can be partly or entirely embodied or supported by one or more suitable software programs, which can be stored on or otherwise provided by any kind of data carrier, and which might be executed in or by any suitable data processing unit. Software programs or routines can be preferably applied in or by the control unit.

BRIEF DESCRIPTION OF DRAWINGS

Other objects and many of the attendant advantages of embodiments of the present invention will be readily appreciated and become better understood by reference to the following more detailed description of embodiments in connection with the accompanied drawings. Features that are substantially or functionally equal or similar will be referred to by the same reference signs.

Figure 1:
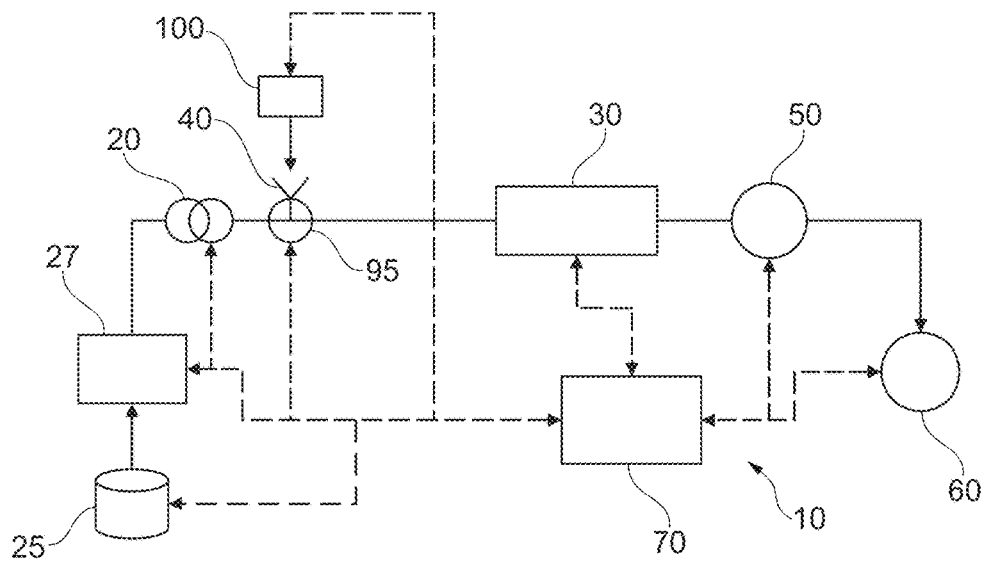
FIG. 1 shows a liquid sample separation system in accordance with embodiments of the present invention, particularly used in high performance liquid chromatography (HPLC).

The illustration in the drawing is schematic.

DETAILED DESCRIPTION

Before describing the figures in further detail, some basic considerations of the present invention will be summarized based on which exemplary embodiments have been developed.

According to an exemplary embodiment of the invention, a punctual junction or temporary fluidic coupling point to a reactor or any other source flow path can be selectively established for branching off a portion of the fluidic sample without disturbing the source flow path.

An embodiment of the invention is hence related to a punctual junction to a reactor. The intention is to draw reactor fluid out of a continuously pumped (for example by reactor pressure) flow without compromising the reactor fluid itself.

In such a configuration, it is possible to draw reactor fluid from a continuously pumped (for example by reactor pressure) reactor. A metering device (or any other embodiment of a volume flow adjustment unit adjusting a volume flow of the fluidic sample to be branched off) can be flushed by itself, with the usage of passive or active valves (for instance a check valve).

A draw or branch off from a continuously pumped reactor fluid as an example for a fluidic sample can be carried out without compromising the source flow path with pressure fluctuations, in particular when using one or more built-in pressure sensors, which provides the opportunity of a precise pre- and/or depressurisation of a loop (as an example for a sample accommodation volume), a needle, a seat and/or the metering device.

In particular it is possible to adjust the speed of drawing or branching off a fluid (such as a fluidic sample) dependent on method requirements (in particular dependent on requirements of a chromatographic separation method, when the branched off fluidic sample is to be separated by liquid chromatography).

Moreover, the usage of a variable sample accommodation volume (such as a loop) for different draw volumes is advantageously possible. Both partial loop fill and (over) filling a fixed loop may be possible in a controlled manner.

Further advantageously, no undesired dilution or contamination of the reactor fluid in the for instance circuit-type source flow path occurs during the time of the established connection. It may then be possible that there are no residues of diluting or contaminating (in particular quenching) solvents which can affect the reactor fluid.

Moreover, fractionation of reactor fluid is possible in certain embodiments.

After sample taking, a precise and automated dilution/quenching of branch of the sample is possible (without contamination of the reactor fluid).

The above mentioned advantages and opportunities can be obtained by a configuration in which one high pressure fluidic valve with corresponding stator/rotor design is provided being switchable into a switching state for reactor junction or branching off of fluidic sample from a source flow path via a switchable or temporarily establishable fluidic coupling point.

In an embodiment, it may be sufficient to provide only one high pressure valve in the sample management device with specifically configured stator/rotor (for instance configured for feed injection) or with a design for classic injection (for instance by flow through injection) for enabling analysis of a reactor fluid in an HPLC system or any other sample separation system.

In terms of pre-compression, a pressure adjustment may be made to prevent an uncontrolled volume stream (caused by a pressure equilibration) at the time of fluidically coupling the source flow path with the volume flow adjustment unit. Furthermore, there is the possibility of a calculation or an implementation of one or more pressure sensors to obtain information used for controlling the pressure adjustment. The usage of the described setup provides a hydraulic junction with the capability to compress and/or decompress loop and/or needle and/or seat with a metering device before and/or after switching into and/or out of the flow path.

Moreover, the metering device may be configured to be self-purgable with fresh solvent which can be provided by one or more solvent containers connected to a solvent selection valve or a solvent container directly connected to the metering device. In addition, any solvent (in particular quenching solvent) can be dispensed via a metering device to control the reactor fluid.

Quench solvent can be dispensed after sample taking, and therefore the reactor fluid may be safely prevented from being affected by contaminants.

A sample management device according to an exemplary embodiment of the invention may be independent of solvents used in the reactor fluid path. The fluidic sample can be taken with marginal influence due to pre- and/or depressurisation of loop, needle, seat and/or metering device.

Two different flow paths (i.e. a first flow path with needle, loop, seat, metering device versus a second flow path in form of the source flow path or reactor fluid path) can work independently, except during the sample taking (i.e. when the fluidic valve of the sample management device is in the branch off state). Therefore, a designer is free to use different solvents in both paths.

Such an embodiment of the invention has advantages: In order to exclude the needle, seat, loop and metering device from the main path of the reactor fluid path, this setup can be advantageously used. The fluidic sample may be taken by a plunger movement of the metering device or other volume flow adjustment unit. The sample draw speed can be adjustable and can be set as method parameter. Automated dilution/quenching of fluidic sample after sample taking is possible without compromising reactor fluid path.

The architecture according to exemplary embodiments of the invention is also compatible with a microreactor configuration. The operating principle is independent of the drawn volume and the ejected volume, which can be variable (i.e., the volume is freely selectable). The ejection may occur in a decoupled state, for instance to transfer the fluidic sample in another sample container or for modifying the sample (for instance by diluting or addition of quenching solvent). It is also possible to eject into the reactor fluid (for instance diluting with a defined volume or addition of quenching fluid). A selectively compressible and decompressible path of needle, seat, loop and metering device is established. Only marginal, if at all, pressure fluctuations may occur due to sample path pre-compression. By pre-compression of the sample loop, pressure fluctuations can be reduced or eliminated. Beyond this, multiple draw actions are possible, with the possibility of a fractionation into the loop. Moreover, low carryover can be obtained in particular due to the provision of a purge position in which also the needle can be lifted to clean the needle-seat interface (with solvent pumped from metering device or an additional flush pump).

The draw volume may be selectable substantially without limitations, in particular may be selectable within a range of a maximum volume of the loop installed. A pressure stable operation is possible, for instance up to 1300 bar or more. The reaction in the reactor can be controlled by feed injection. It is also possible to dispense control fluids into the reactor fluid path/source flow path.

Referring now in greater detail to the drawings, FIG. 1 depicts a general schematic of a liquid sample separation system 10 according to an exemplary embodiment of the invention. A pump as fluid drive 20 receives a mobile phase from a solvent supply 25, typically via a degasser 27, which degases and thus reduces the amount of dissolved gases in the mobile phase. The mobile phase drive or fluid drive 20 drives the mobile phase through a separation unit 30 (such as a chromatographic column) comprising a stationary phase. A sampler or injector 40, implementing a fluidic valve 95, can be provided between the fluid drive 20 and the separation unit 30 in order to subject or add (often referred to as sample introduction) a sample fluid into the mobile phase. The stationary phase of the separation unit 30 is configured for separating compounds of the sample liquid. A detector 50 is provided for detecting separated compounds of the sample fluid. A fractionating unit 60 can be provided for outputting separated compounds of sample fluid.

While the mobile phase can be comprised of one solvent only, it may also be mixed from plural solvents. Such mixing might be a low pressure mixing and provided upstream of the fluid drive 20, so that the fluid drive 20 already receives and pumps the mixed solvents as the mobile phase. Alternatively, the fluid drive 20 might be comprised of plural individual pumping units, with plural of the pumping units each receiving and pumping a different solvent or mixture, so that the mixing of the mobile phase (as received by the separation unit 30) occurs at high pressure and downstream of the fluid drive 20 (or as part thereof). The composition (mixture) of the mobile phase may be kept constant over time, the so called isocratic mode, or varied over time, the so called gradient mode.

A data processing unit or control unit 70, which can be a PC or workstation, may be coupled (as indicated by the dotted arrows) to one or more of the devices in the sample separation system 10 in order to receive information and/or control operation. For example, the control unit 70 may control operation of the control unit 20 (e.g. setting control parameters) and receive therefrom information regarding the actual working conditions (such as output pressure, etc. at an outlet of the pump 20). The control unit 70 may also control operation of the solvent supply 25 (e.g. setting the solvent/s or solvent mixture to be supplied) and/or the degasser 27 (e.g. setting control parameters such as vacuum level) and might receive therefrom information regarding the actual working conditions (such as solvent composition supplied over time, vacuum level, etc.). The control unit 70 might further control operation of the sampling unit or injector 40 (e.g. controlling sample injection or synchronization of sample injection with operating conditions of the fluid drive 20). The separation unit 30 might also be controlled by the control unit 70 (e.g. selecting a specific source flow path or column, setting operation temperature, etc.), and send—in return—information (e.g. operating conditions) to the control unit 70. Accordingly, the detector 50 might be controlled by the control unit 70 (e.g. with respect to spectral or wavelength settings, setting time constants, start/stop data acquisition), and send information (e.g. about the detected sample compounds) to the control unit 70. The control unit 70 might also control operation of the fractionating unit 60 (e.g. in conjunction with data received from the detector 50) and provide data back.

As illustrated schematically in FIG. 1, the fluidic valve 95 and the injector 40 may cooperate with a sample management device 100 (embodiments of which being described in the following figures) which may branch off a fluidic sample from a source flow path (not shown in FIG. 1) for separation by the sample separation system 10. The control unit 70 may also control operation of the sample management device 100. Hence, FIG. 1 indicates that the injector 40 of the sample separation system 10 according to FIG. 1 can be embodied as sample management device 100, or as part thereof, or may functionally cooperate with a sample management device 100.

Figure 2:
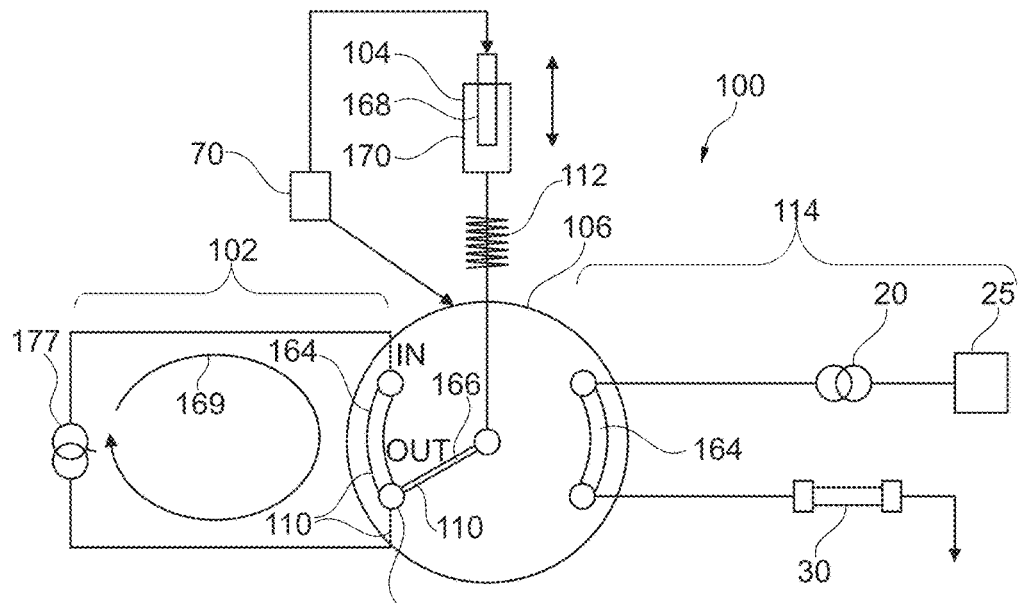
FIG. 2 illustrates a sample management device according to an exemplary embodiment of the invention in a switching state.
Figure 3:
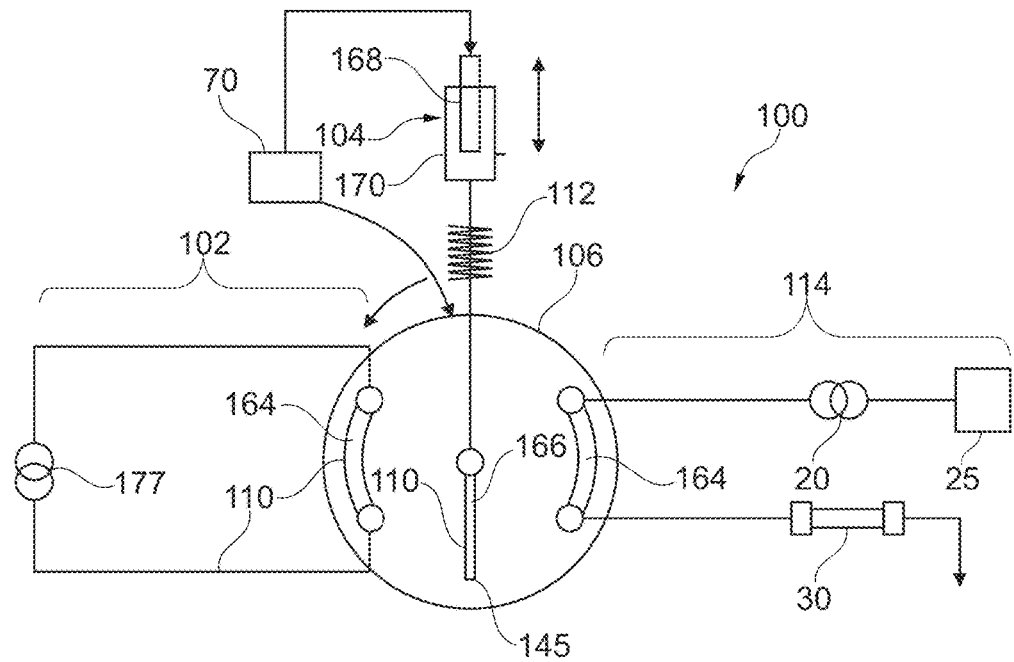
FIG. 3 illustrates the sample management device in another switching state.
Figure 4:
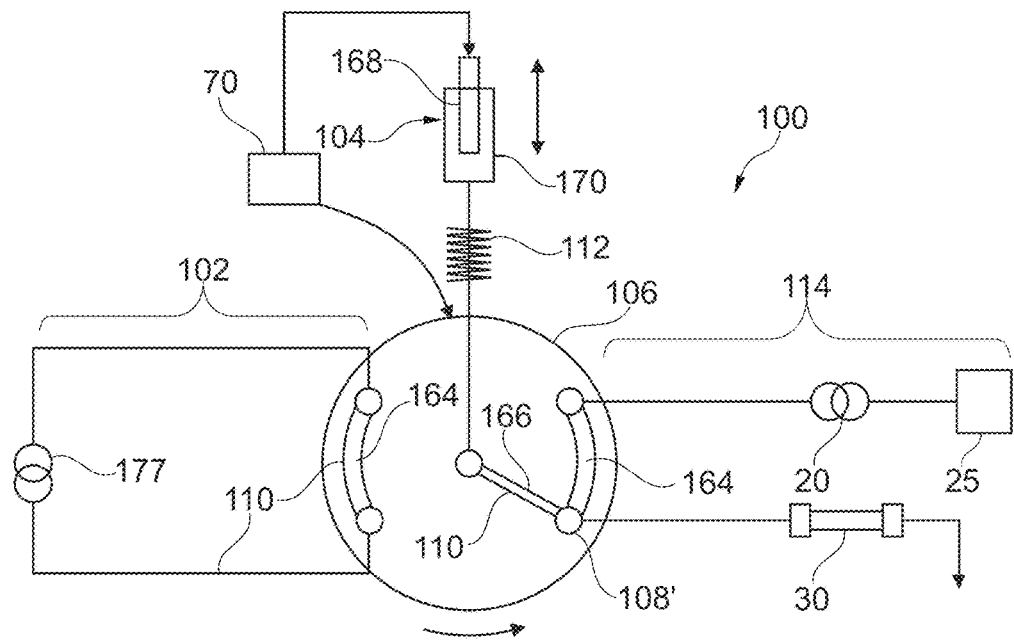
FIG. 4 illustrates the sample management device in another switching state.

FIG. 2 to FIG. 4 illustrate a sample management device 100 according to an exemplary embodiment of the invention in different switching states.

Referring to FIG. 2, sample management device 100 is provided with a source flow path 102 in which a fluidic sample can flow. In FIG. 2, the source flow path 102 can be any kind of process which processes a fluidic sample, for instance a continuous beverage production system. Within such a source flow path 102, a fluid drive 177 (such as a fluid pump) may be arranged for driving the fluidic sample along the source flow path 102. In the shown embodiment, the source flow path 102 is configured for closed-loop fluid processing which is indicated schematically in FIG. 2 by reference numeral 169. Moreover, the sample management device 100 comprises a volume flow adjustment unit 104 configured for adjusting a volume or volume flow of the fluidic sample to be branched off from the source flow path 102 at a temporary fluidic coupling point 108. A fluidic valve 106 is fluidically coupled with the source flow path 102 and with the volume flow adjustment unit 104.

Advantageously, the fluidic valve 106 is switchable into a branch off state (as shown in FIG. 2) in which the temporary (i.e. only present in the branch off state, while being absent in other switching states of the fluidic valve 106, compare FIG. 3 and FIG. 4) fluidic coupling point 108 is established as T-junction within (or is generated as T-junction within) the source flow path 102 to branch off an adjustable volume of the fluidic sample from the source flow path 102 via the fluidic coupling point 108 while a flow of the fluidic sample within the source flow path 102 continues. In the shown configuration, the fluidic coupling point 108 is fluidically coupled into the source flow path 102 and into a volume flow adjustment path guiding to the volume flow adjustment unit 104 as a consequence of this switching operation. Advantageously, the fluidic valve 106 is configured so that a flow of the fluidic sample in the source flow path 102 continues substantially undisturbed and uninterruptedly in the branch off state. As can be taken from FIG. 2, the fluidic coupling point 108 is located as a fluidic port in an interior of the fluidic valve 106. As can furthermore be taken from FIG. 2, the fluidic valve 106 is configured so that the volume flow adjustment unit 104 is fluidically coupled with the source flow path 102 via the fluidic coupling point 108. The latter has three fluid connections 110 defined by the fluidic valve 106 in the branch off state. Two of the three fluid connections 110 at the fluidic coupling point 108 are fluidically coupled to the source flow path 102 (or form part thereof), and another one of the three fluid connections 110 is fluidically coupled to the volume flow adjustment unit 104 (or forms part of the volume flow adjustment path). The three fluid connections 110 correspond to two valve-internal fluidic conduits and one valve-external fluidic conduit, which are fluidically coupled with one another at the fluidic coupling point 108 in the branch off state. More precisely, one fluidic conduit (see stator groove 164) relates to a stator and one fluidic conduit (see rotor groove 166) relates to a rotor of the fluidic valve 106. The fluidic coupling point 108 corresponds to or is positioned at a fluid port of the stator of the fluidic valve 106.

According to FIG. 2, the volume flow adjustment unit 104 comprises an adjustment pump in form of a piston-driven metering pump being configured for adjusting the volume flow of the fluidic sample to be branched off from the source flow path 102 (wherein a pumping pressure may be measured by one or more pressure sensors, not shown in FIG. 2, wherein the measured pressure may be used for control purposes). More specifically, the volume flow adjustment unit 104 is configured for adjusting the volume of the fluidic sample to be branched off from the source flow path 102 by piston motion. As can be taken from FIG. 2, the volume of the fluidic sample branched off from the source flow path 102 flows into a sample accommodation volume 112, which can be embodied as a sample loop.

The sample management device 100 according to FIG. 2 furthermore has a destination flow path 114 which is also fluidically coupled with other ports of the fluidic valve 106. The fluidic valve 106 is switchable into a sample supply state, shown in FIG. 4, in which the previously branched off fluidic sample is supplied into the destination flow path 114. Hence, the destination flow path 114 may be configured as a liquid chromatography sample separation unit which is capable of separating a branched off fluidic sample into fractions.

Hence, the volume flow adjustment unit 104 is here embodied as a metering pump having a piston 168 reciprocating in a piston chamber 170, controlled by control unit 70. For instance, by moving upwardly according to FIG. 2, the piston 170 may draw or intake a fluidic sample into the sample accommodation volume 112. By moving downwardly referring to FIG. 2, the piston 170 may inject a previously intaken fluidic sample, which has been temporarily stored in the sample accommodation volume 112, towards and into the destination flow path 114. The destination flow path 114 is here configured for liquid chromatography separation of the injected branched off fluidic sample, as indicated by members 25, 20, 30 described in FIG. 1.

In order to activate the branch off state shown in FIG. 2, the rotor of fluidic valve 106 is switched so that the rotor groove 166 is fluidically coupled with the stator groove 164 so that the fluidic coupling point 108 is generated or established. Thus, the fluidic coupling point 108 as fluidic T-piece is temporarily established, i.e. limited to a certain switching state of the fluidic valve 106. Depending on the conditions in the source flow path 102 and the conditions in the fluidic conduit connecting the fluidic coupling point 108 with the volume flow adjustment unit 104, it is defined which amount of fluidic sample is split at the fluidic coupling point 108 and branched off into the sample accommodation volume 112. During this branching off or splitting of the flow, the pressure conditions and the entire process in the source flow path 102 remain undisturbed.

According to FIG. 2, the fluidic valve 106 has:
- a source flow-in port (see reference numeral IN) through which the fluidic sample can be guided to flow from the source flow path 102 into the fluidic valve 106;
- a source flow-out port (see reference numeral OUT, which is here equivalent to the fluidic coupling point 108) through which branched off fluidic sample can flow away from the source flow path 102, and not-branched off fluidic sample can simultaneously remain flowing within the source flow path 102; and
- a branch off port (i.e. the central port of the fluidic valve 106) through which the branched off fluidic sample can flow to sample accommodation volume 112 in fluid communication with the volume flow adjustment unit 104.

As mentioned, the fluidic valve 106 shown in FIG. 2 is configured as a rotor switch valve comprising rotor and stator being rotatable relative to one another. In the shown configuration, the stator comprises a plurality of ports and stator grooves 164 as fluid connections between respective ones of the various ports. Furthermore, the rotor comprises rotor groove 166 which can be brought in fluid communication or out of fluid communication with individual ones of the ports and stator grooves 164 of the stator.

FIG. 3 shows the sample supply device 100 according to FIG. 2 in an intermediate switching state in which the rotor has been further rotated counter clockwise so that the rotor groove 166 is now fluidically decoupled from both stator grooves 164. For example, in the shown switching position, a flushing task may be executed, if desired. Also a compression/decompression task is executable. A channel end point 145 of the rotor groove 166 is now a fluidically unconnected dead end. Fluidic coupling point 108 is no longer present or established.

As can be taken from FIG. 4, the sample supply device 100 has been further switched to a supply switch state by further rotating the rotor counter clockwise relative to the stator so as to bring the rotor groove 166 in alignment with one of the ports on the right-hand side of FIG. 4. By taking this measure, movement of the piston 168 in the piston chamber 170 of the volume flow adjustment unit 104 may inject the previously branched off fluidic sample from the sample accommodation volume 112 into the destination flow path 114 for liquid chromatography separation. More precisely, the fluidic sample is injected from the sample accommodation volume 112 into the destination flow path 114 via a further temporary fluidic coupling point 108'. When the fluidic coupling point 108 is established, the further fluidic coupling point 108' is not established, and vice versa. A respective position of the channel end point 145 defines whether the fluidic coupling point 108 is established within the source flow path 102, or whether the further fluidic coupling point 108' is established within the destination flow path 114.

Referring to both switching states according to FIG. 3 and FIG. 4, the fluidic valve 106 is switchable in either of these switching states for further processing the branched off fluidic sample in which the fluidic coupling point 108 is eliminated. By establishing the T-piece type fluidic coupling point 108 only temporarily, i.e. only in the branch off state according to FIG. 2, fluidic sample processing in the source flow path 102 remains undisturbed while further processing the branched off fluidic sample in a separate flow path according to FIG. 3 or FIG. 4.

Figure 5:
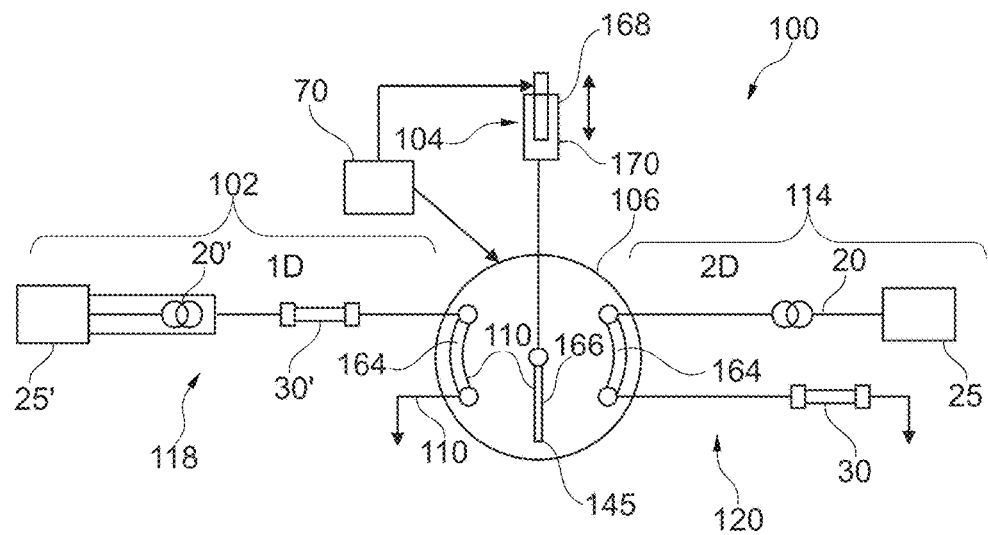
FIG. 5 illustrates a sample management device according to another exemplary embodiment of the invention.
Figure 6:
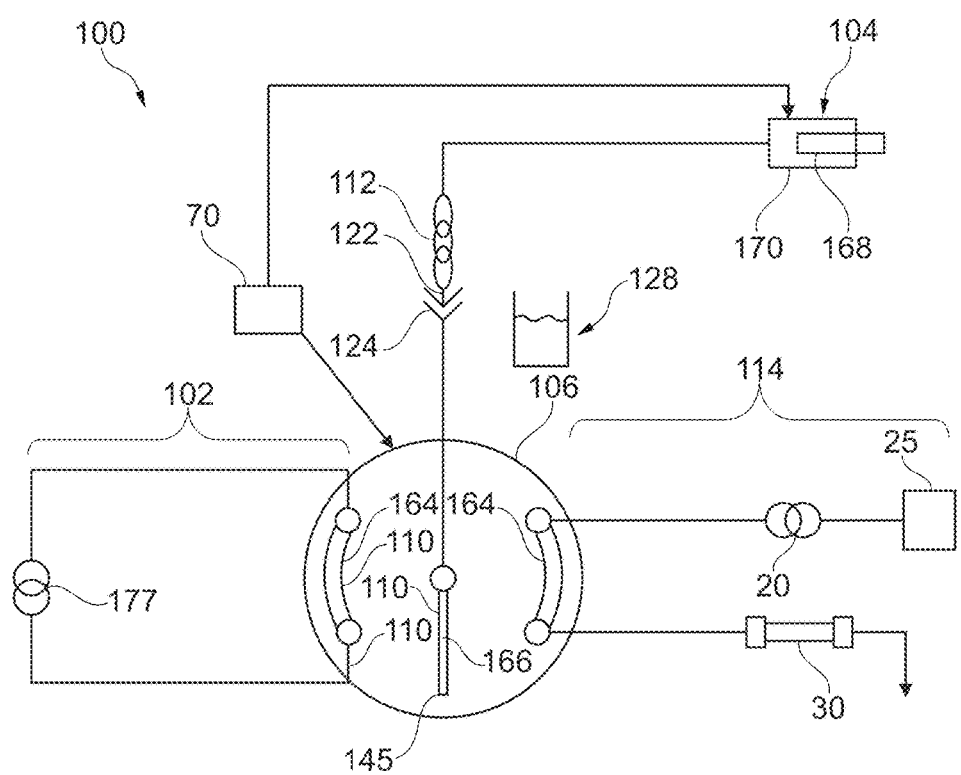
FIG. 6 illustrates a sample management device according to another exemplary embodiment of the invention.

FIG. 5 and FIG. 6 illustrate sample management devices 100 according to other exemplary embodiments of the invention.

Referring to FIG. 5, the source flow path 102 comprises a sample separation apparatus 118 for separating the fluidic sample in fractions. Moreover, the destination flow path 114 comprises a further sample separation apparatus 120 for further separating the fractions in sub-fractions.

The embodiment according to FIG. 5 differs from the embodiment according to FIG. 2 to FIG. 4 in that according to FIG. 5, the source flow path 102 is configured as a liquid chromatography separation apparatus in which the fluidic sample is separated into fractions. Thus, the source flow path 102 here constitutes a first dimension (see reference numeral 1D) of a two-dimensional sample separation apparatus, wherein reference numerals 25, 20, 30 and reference numerals 25', 20', 30' indicate corresponding fluidic members. The separated fractions of the sample may be, one after the other, temporarily stored in the fluidic conduit connected to the volume flow adjustment unit 104, and can later on be injected into the destination flow path 114 for further separation in a second dimension (see reference numeral 2D) of the two-dimensional sample separation apparatus.

Referring to FIG. 6, the sample management device 100 comprises a needle 122, a seat 124 and an accommodation volume 112 between the volume flow adjustment unit 104 and the fluidic valve 106. The needle 122 is drivable selectively into the seat 124 or out of the seat 124 for transferring a substance from the accommodation volume 112 to an external entity 128 (which is here embodied as a fluid container), or vice versa.

The embodiment of FIG. 6 differs from the embodiment of FIG. 2 to FIG. 4 in that the fluidic path next to the volume flow adjustment unit 104 is configured as an injector. A fluidic sample branched off from the source flow path 102 and being presently stored in the sample accommodation volume 112 can be transferred from there into entity 128 by driving the needle 122 out of the seat and into the entity 128 and by subsequently forwarding the piston 168 in the piston chamber 170 for pressing the branched off fluidic sample from the sample accommodation volume 112 into the entity 128. A fluid may also be transferred from entity 128 into accommodation volume 112 by an inverse piston motion (for instance for diluting a fluidic sample). With the configuration according to FIG. 6, it is hence possible to intake a fluid into the accommodation volume 112 or to eject a fluid from the accommodation volume 112 to a desired destination.

FIG. 7 to FIG. 11 illustrate a sample management device 100 forming part of a sample separation system 10 according to another exemplary embodiment of the invention in different switching states. In the following, operation of the sample separation system 10 shown in FIG. 7 to FIG. 11 will be explained.

The sample separation system 10 is configured for separating a fluidic sample and comprises fluid drive 20 (such as a high pressure pump) configured for driving a mobile phase, separation unit 30 (such as a chromatographic column) configured for separating the fluidic sample in the mobile phase, and sample management device 100 for branching off an adjusted volume the fluidic sample for injection between the fluid drive 20 and the separation unit 30. According to FIG. 7 to FIG. 11, the source flow path 102 comprises a fluid reactor 116 for subjecting the fluidic sample to a reaction (such as a chemical or biological reaction). A sample separation apparatus 130, including inter alia the fluid drive 20 and the separation unit 30, is provided, into which the branched off fluidic sample is injectable from external entity 128, such as a vial. Furthermore, the sample separation apparatus 130 comprises a further needle 132, a further seat 134 and a further accommodation volume 136. The further needle 132 is drivable selectively into the further seat 134 or out of the further seat 134 for transferring the branched off fluidic sample from the external entity 128 into the further accommodation volume 136 for subsequent injection, via fluidic valve 95, between fluid drive 20 and separation unit 30 for sample separation.

Figure 7:
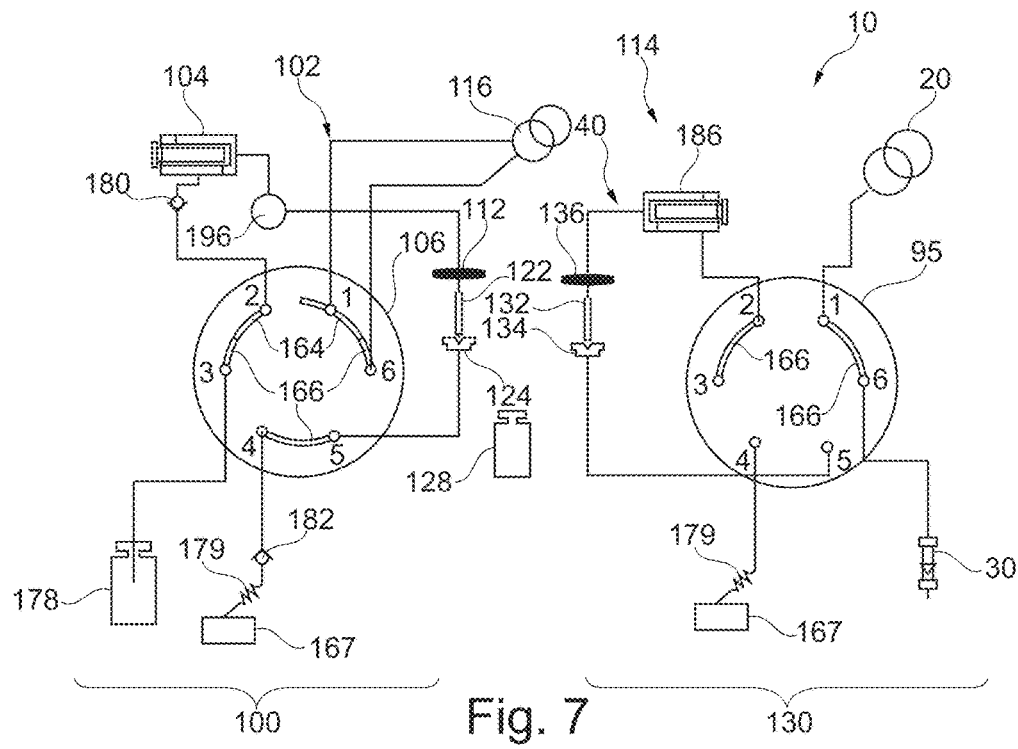
FIG. 7 illustrates a sample separation system with a sample management device according to another exemplary embodiment of the invention in an operation mode or switching state.

On the left-hand side of FIG. 7, a fluid reactor circuit is shown. A fluidic sample processed in fluid reactor 116 can be branched off using the principle described above referring to FIG. 2 to FIG. 4 via a temporary fluidic coupling point 108 shown in FIG. 9. In the switching state according to FIG. 7 however, a reactor pump of the fluid reactor 116 pumps the fluidic sample along a circular path including ports 1 and 6 of the fluidic valve 106 as well as grooves 164, 166 bridging these ports 1, 6. A port 4 is connected via a fluidic restriction 179 towards a waste 167. Furthermore, fluidic ports 4 and 5 are coupled by a further groove 166 and are connected to seat 124, needle 122 and sample accommodation volume 112 to volume flow adjustment unit 104 configured as metering pump. The latter is presently in fluid communication via ports 2, 3 and further grooves 164, 166 of the fluidic valve 106 with a solvent container 178. As can be furthermore taken from the left-hand side of FIG. 7, two check valves 180, 182 are implemented, one between the fluidic restriction 179 and port 4, and the other one between the volume flow adjustment unit 104 and port 2. A pressure sensor is denoted with reference numeral 196.

The sample separation system 10 shown on the left-hand side of FIG. 7 is presently inactive in the configuration according to FIG. 7. Mobile phase drive 20 may drive fluidic sample through fluidic valve 95 and from there to separation unit 30. A metering device 186 is coupled via further accommodation volume 136, further needle 132 and further seat 134 to port 5 of the fluidic valve 95. A further flow path with a fluid restriction 179 and a waste 167 are shown as well.

In the configuration according to FIG. 7, the fluidic valve 106 is in the reactor drainage state. The reactor 116 and connected fluid conduits carry out a circular flow process during which a reaction takes place with the fluidic sample in the circular flow path including the reactor 116. In parallel, a solvent can be filled in from the solvent container 178 into the sample accommodation volume 112. This solvent is transported by a motion of the piston 168 of the volume flow adjustment unit 104 so that solvent flows from the solvent container 178 via port 3, grooves 164, 166 connecting ports 3 and 2, port 2, volume flow adjustment unit 104, pressure sensor 196 and from there into the sample accommodation volume 112. For example, this solvent intake process may help to dilute the fluidic sample with any desired dilution ratio, even with very small amounts of fluidic sample. For instance, 499 µl of solvent may be intaken into the sample accommodation volume 112 which may have a capacity of for instance 500 µl. Thus, the fluidic valve 106 is, according to FIG. 7, in a purge reactor position and pre-fill dilution solvent position. The purge position corresponds to the fluidic path including sample accommodation volume 104, needle 122, seat 124, volume flow adjustment unit 104. The sample accommodation volume 112 may hence be filled with a calculated amount of dilution solvent after purge. The dilution solvent may be filled into the container 178 (such as a vial) to provide target volumes greater than 500 µl.

Figure 8:
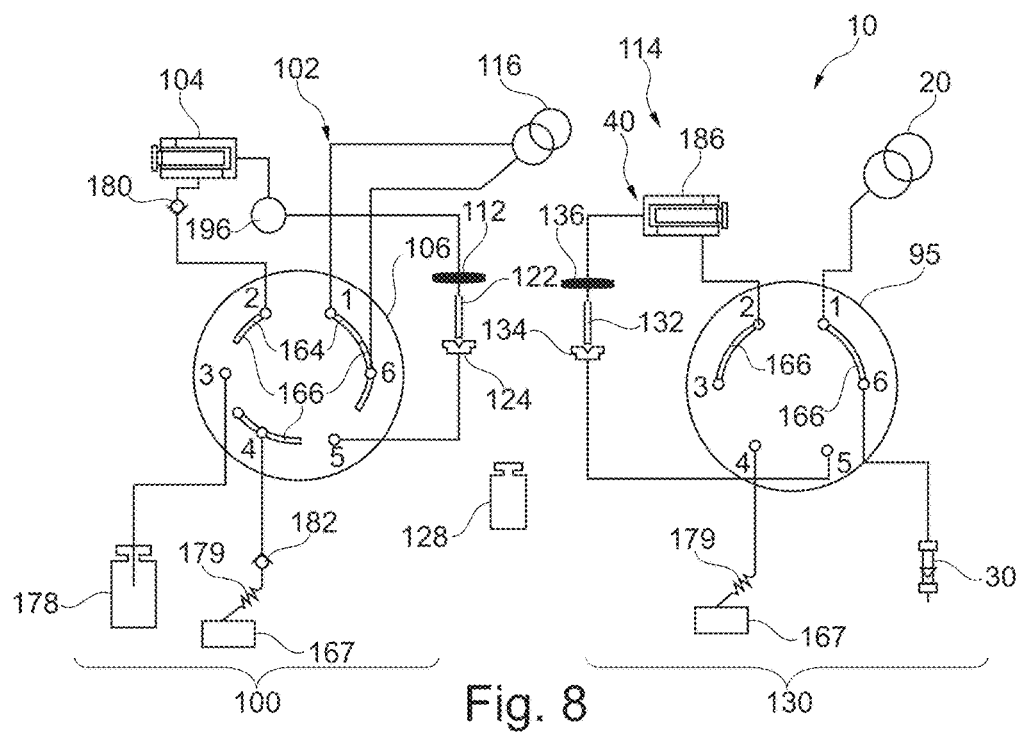
FIG. 8 illustrates the sample separation system with the sample management device in another switching state.

Referring to FIG. 8, the fluidic valve 106 is switchable in a pressure adjustment state in which the source flow path 102 is fluidically decoupled from the volume flow adjustment unit 104 and in which the volume flow adjustment unit 104 is operable for adjusting a pressure between the volume flow adjustment unit 104 and the fluidic valve 106. In particular, the volume flow adjustment unit 104 is operable for adjusting the pressure in the pressure adjustment state to reduce a pressure difference with regard to another pressure in the source flow path 102 prior to switching the fluidic valve 106 in the branch off state (see FIG. 9).

Still referring to FIG. 8, the fluidic valve 106 has been switched into pre-compression mode. In the pre-compression mode according to FIG. 8, the circular flow involving the reactor 116 remains the same as in FIG. 7. However, now a flow connection with two unconnected ends from port 2 through volume flow adjustment unit 104, sample accommodation volume 112, needle 124, seat 122 up to port 5 is established. By moving the piston 168 of the volume flow adjustment unit 104, the pressure within the described blocked flow path can be increased to a predefined value, for instance from atmospheric pressure to 100 bar. 100 bar may be the pressure in the circular reactor path involving the reactor 116. Thus, the flow path of sample accommodation volume 112, needle 124, seat 122 and volume flow adjustment unit 104 is blocked. The described blocked flow path may be compressed to reactor pressure (wherein pressure can be sensed and monitored using the pressure sensor 196). The mode according to FIG. 8 can be denoted as reactor drainage mode with a de/compressed position in order to compress to reactor pressure, if desired. It is possible that a quench solution is drawn from a vial position.

Figure 9:
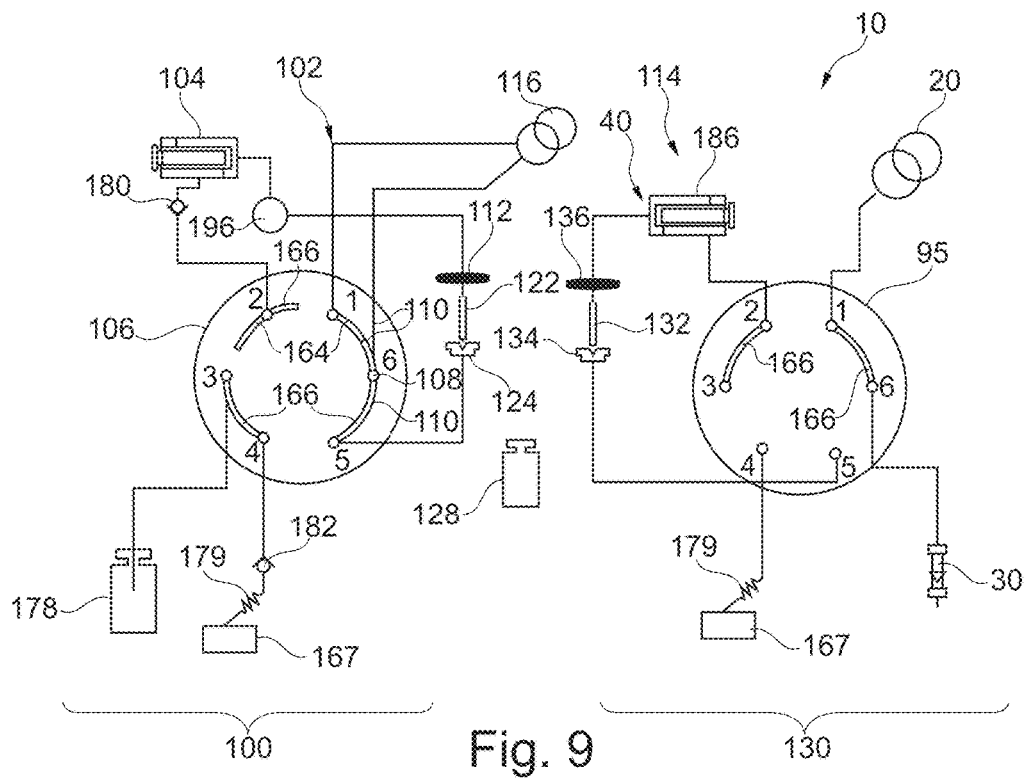
FIG. 9 illustrates the sample separation system with the sample management device in another switching state.

Now referring to FIG. 9, a predefined amount of fluidic sample may be drawn or branched off from the reactor circuit into the sample accommodation volume 112. For this purpose, the fluidic valve 106 has been switched into the branch off state shown in FIG. 9 (which corresponds to FIG. 2). The circular flow within the reactor path involving the reactor 116 is only very slightly disturbed, since a small portion of the fluidic sample is branched off at fluidic coupling point 108 towards port 5 and from there through seat 124 and needle 122 into sample accommodation volume 112. The undisturbed branching off of the predefined amount of fluidic sample is controlled by the pressure applied by the volume flow adjustment unit 104, which can be sensed by pressure sensor 196. Sensed pressure can be used for monitoring and controlling or even regulating purposes. By pressure control, it can be ensured that the influence of the branch off procedure on the source flow path 102 remains neglectably low.

Advantageously, sample may be drawn up to an extent that the sample accommodation volume 112 is subsequently fully filled. It is recalled that already 499 μl of solvent are located here. Hence, by drawing 1 μl of the fluidic sample into the sample accommodation volume 112, its amount can be precisely controlled and its dilution ratio with solvent can be controlled as well with high accuracy.

In the state according to FIG. 9, the system assumes a draw position in which a predefined amount of fluidic sample can be branched off from the reactor 116 without disturbing the process in the circular reactor path. In the configuration according to FIG. 9, the sample accommodation volume 112, the needle 124, the seat 122 and the volume flow adjustment unit 104 are connected to the reactor 116 via junction or fluidic coupling point 108 which has meanwhile been established within the reactor flow path, i.e. within source flow path 102. The establishing of the fluidic coupling point 108 fluidically switches together the source flow path 102 with the volume flow adjustment unit 104. A predefined amount of fluidic sample may be guided out of the reactor circuit without disturbing the reactor circuit.

Figure 10:
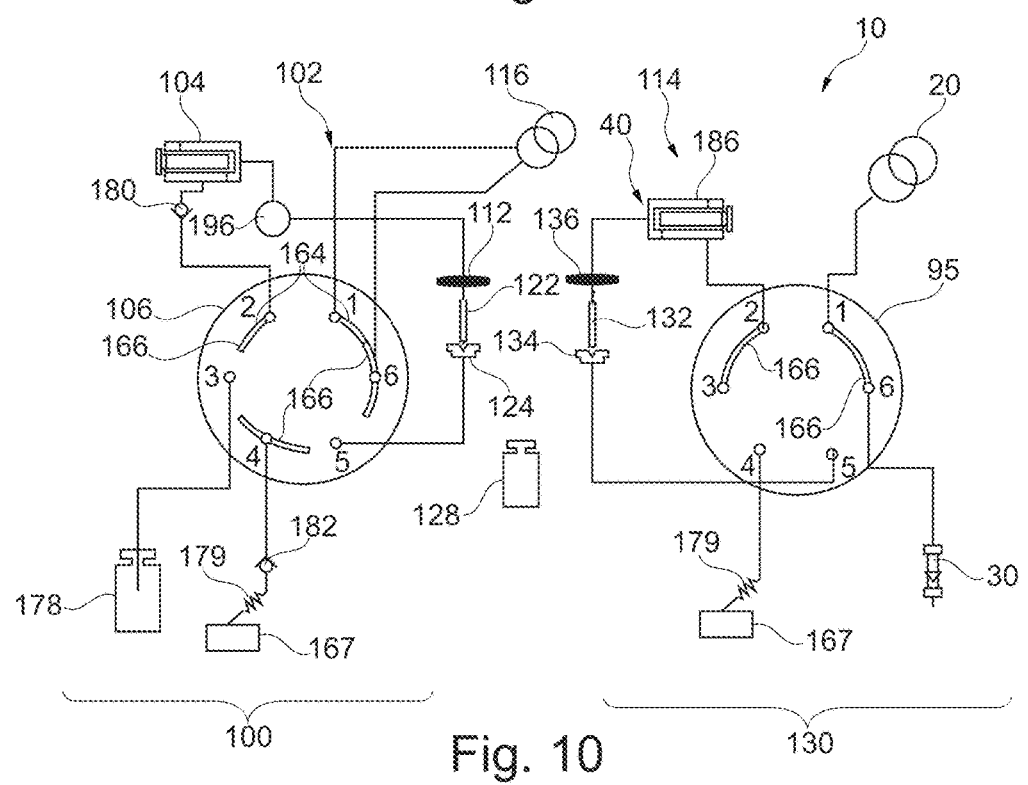
FIG. 10 illustrates the sample separation system with the sample management device in another switching state.

Referring to FIG. 10, the system has been transferred into a further decompression state. If desired, the pressure inside the again blocked fluidic path involving the volume flow adjustment unit 104 can be reduced, for instance to atmospheric pressure. In parallel to this and completely undisturbed and uninterrupted by the fluid draw process described above, the fluidic sample remaining in the reactor circuit or source flow path 102 continuously flows uninterruptedly.

Figure 11:
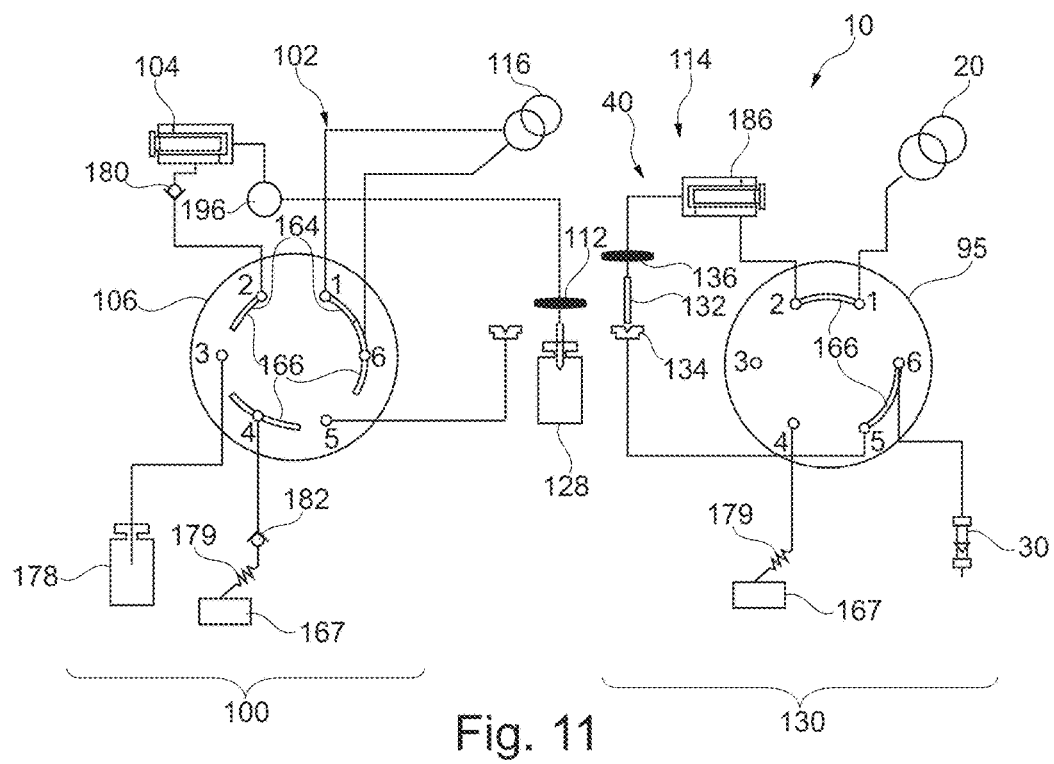
FIG. 11 illustrates the sample separation system with the sample management device in another switching state.

FIG. 11 now shows an operation mode in which the fluidic sample which has been intaken from the reactor circuit and which has been diluted with the solvent is filled into container or entity 128. For this purpose, the needle 122 is driven out of the seat 124 and into the container-type entity 128. Subsequently, the further needle 132 can be driven out of the further seat 134 and may be immersed into the diluted fluidic sample in the entity 128. After this, the diluted fluidic sample branched off from the source flow path 102 is located in the further sample accommodation volume 136 and can be separated by the sample separation system 10. For this purpose, the fluidic valve 95 can be switched into a position in which the mobile phase drive 20 drives the branched of and transferred fluidic sample from the further sample accommodation volume 136 towards the sample separation unit 30, such as a chromatographic separate column.

Figure 12:
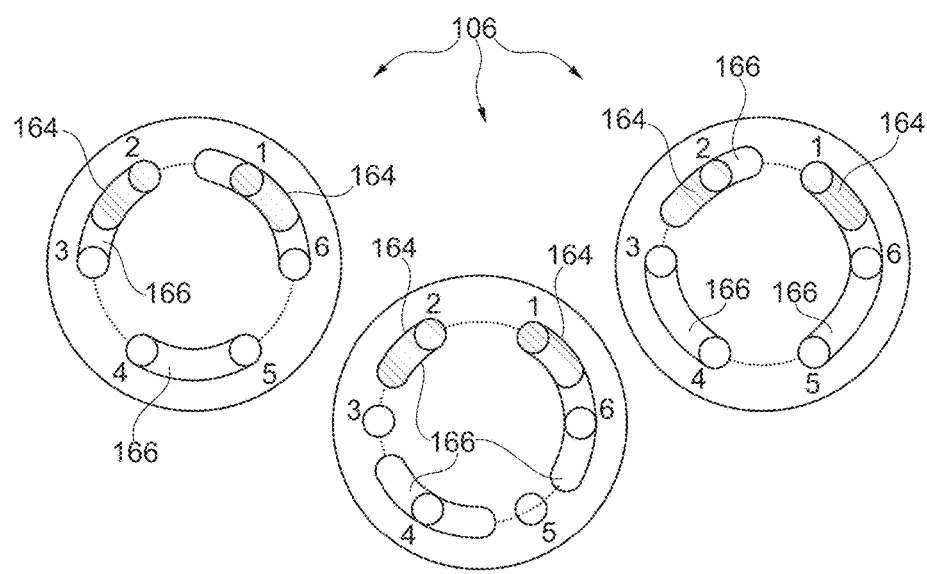
FIG. 12 shows ports and grooves of a stator and a rotor of a fluidic valve according to FIG. 7 to FIG. 11.

FIG. 12 shows ports 1 to 6 and grooves 164, 166 of a stator and a rotor of the fluidic valve 106 according to FIG. 7 to FIG. 11.

More specifically, FIG. 12 shows the fluidic valve 106 described above in three different switching states. As described above, the fluidic valve 106 is formed by a stator and a rotor, wherein the stator has ports 1 to 6 and also has two stator grooves 164. Moreover, the rotor has three rotor grooves 166 according to FIG. 12. With this configuration, all required switching states of the sample management system 100 may be served by only a single fluidic valve 106.

Figure 13:
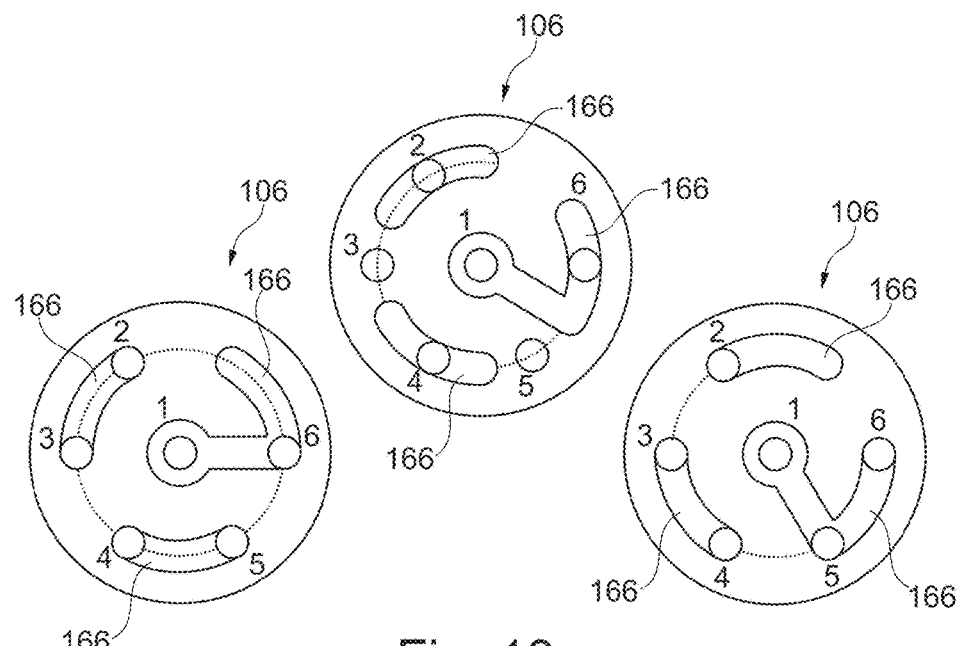
FIG. 13 illustrates a fluidic valve of a sample management device without stator grooves according to another exemplary embodiment of the invention.

FIG. 13 illustrates a fluidic valve 106 of a sample management device 100 without stator grooves 164 according to another exemplary embodiment of the invention.

FIG. 13 shows an alternative configuration of the fluidic valve 106 in which the stator comprises only ports 1 to 6, but is free of stator grooves 164. The rotor comprises three rotor grooves 166 configured in the way as shown in FIG. 13. By taking this measure, all switching states required for operation of the sample management device 100 may be provided by a single fluidic valve 106, without the necessity of providing stator grooves 164. However, the embodiment of FIG. 12 has the advantage of an even smaller dead volume.

FIG. 14 to FIG. 21 illustrate sample management devices 100 according to other exemplary embodiments of the invention. These embodiments show that very different valve configurations and fluidic applications are possible with embodiments of the invention.

Figure 14:
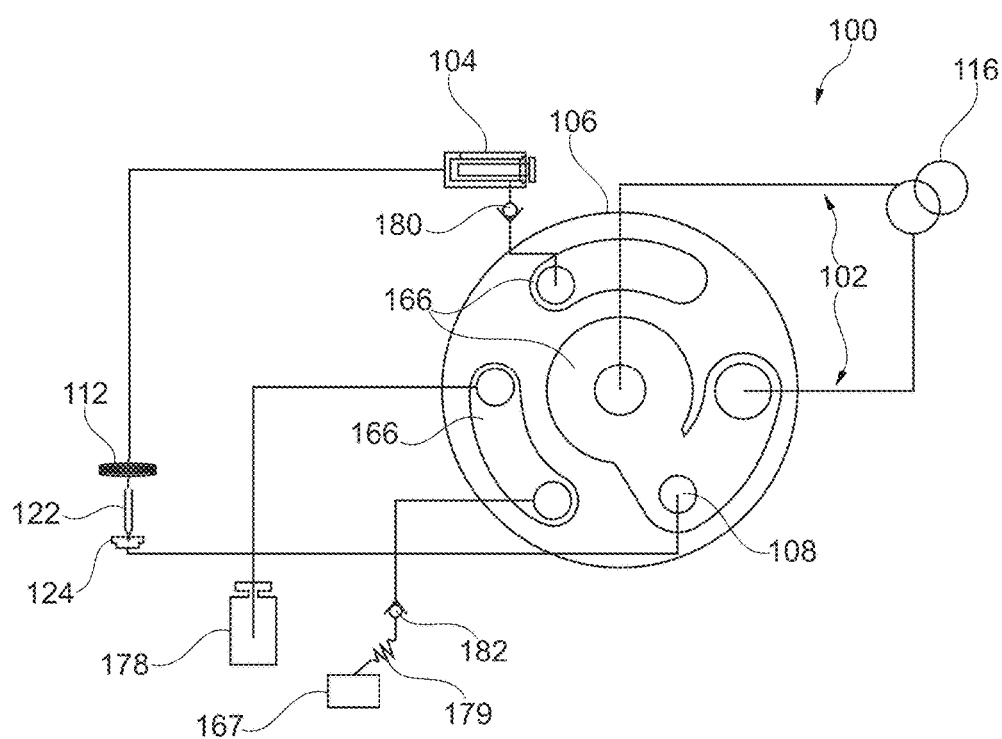
FIG. 14 illustrates a sample management device according to another exemplary embodiment of the invention.

According to FIG. 14, a sample management device 100 for preparation applications (for instance with >10 ml/min) is shown which has a fluidic valve 106 being free of stator grooves 164.

Figure 15:
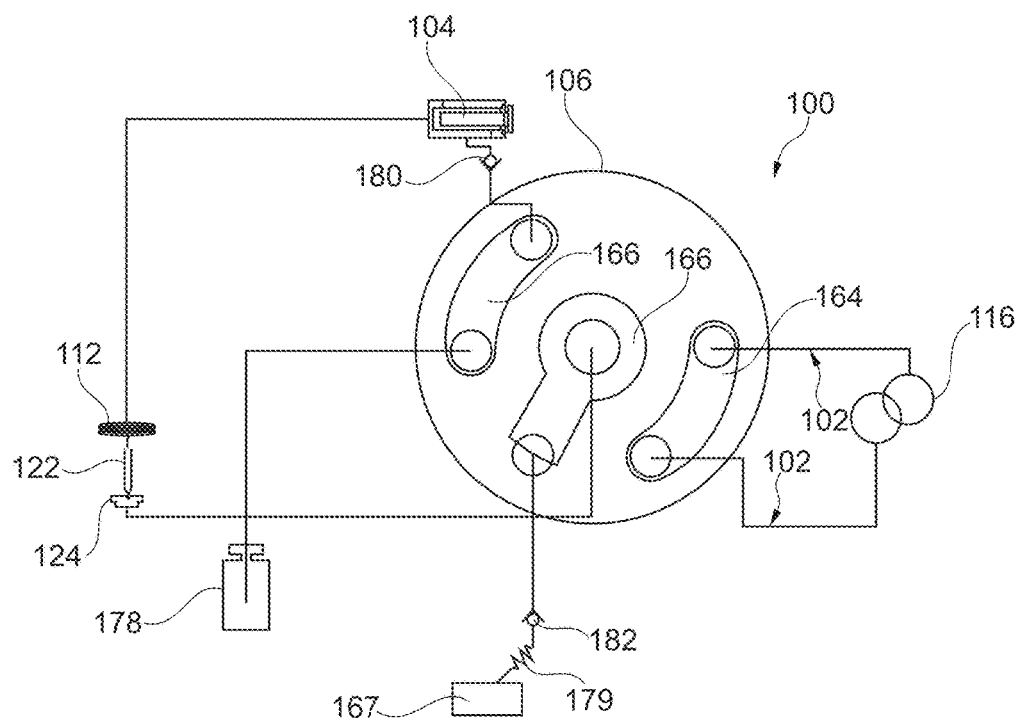
FIG. 15 illustrates a sample management device according to another exemplary embodiment of the invention.

According to FIG. 15, a sample management device 100 for preparation applications is shown which has a fluidic valve 106 comprising a stator groove 164.

Figure 16:
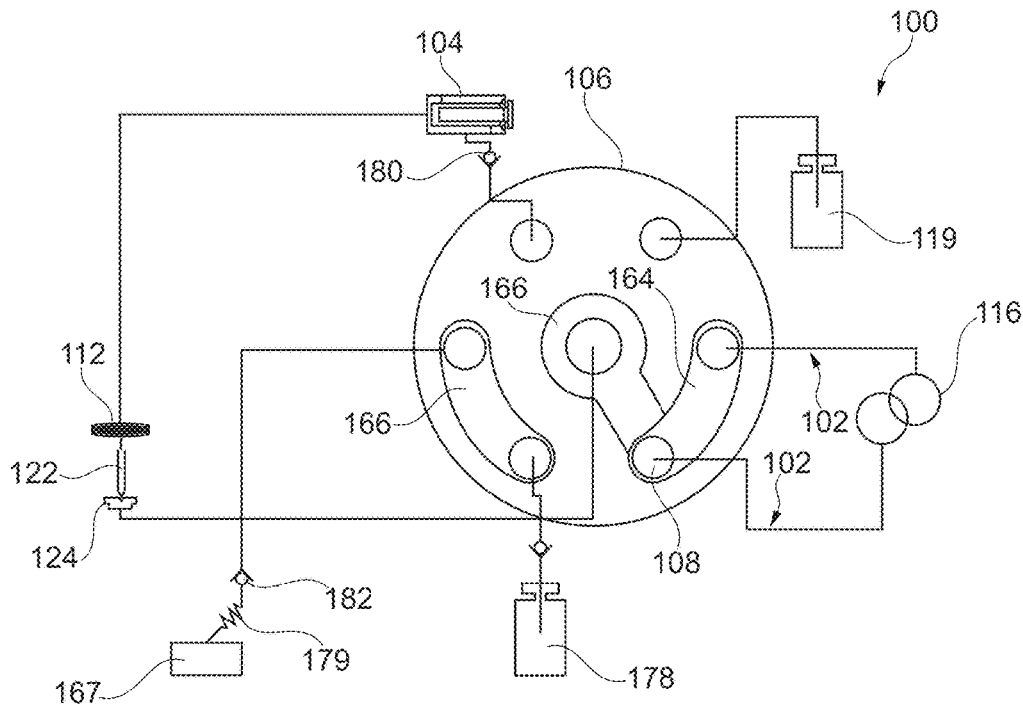
FIG. 16 illustrates a sample management device according to another exemplary embodiment of the invention.

According to FIG. 16, a sample management device 100 for preparation applications is shown which has a fluidic valve 106 comprising a stator groove 164. A further vial 119 is foreseen according to FIG. 16.

Figure 17:
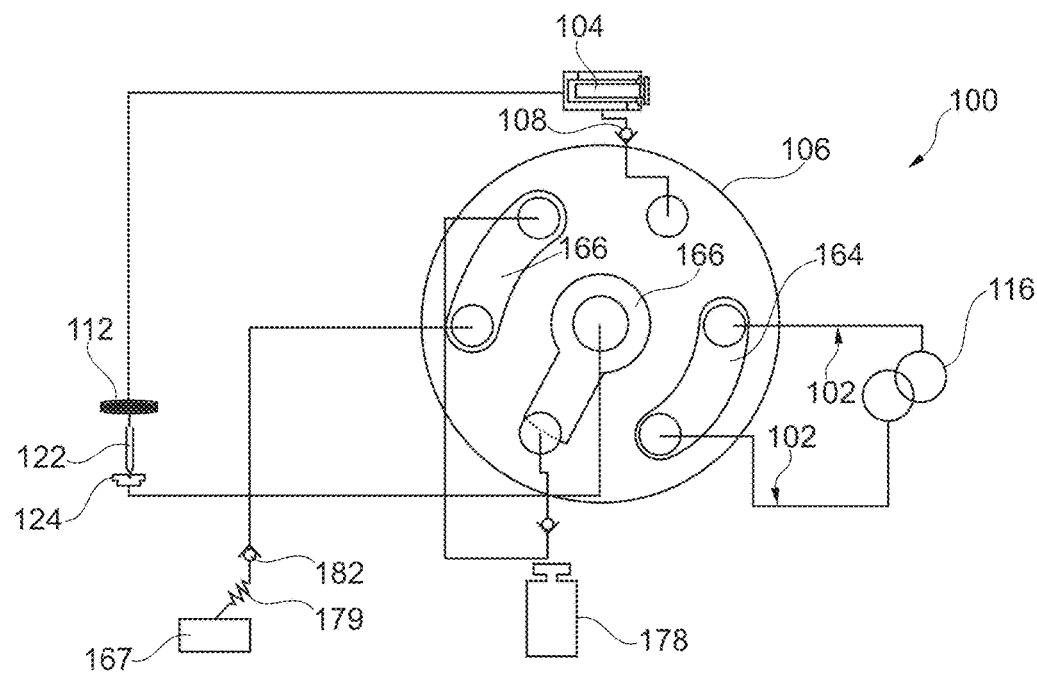
FIG. 17 illustrates a sample management device according to another exemplary embodiment of the invention.

According to FIG. 17, a sample management device 100 for preparation applications is shown which has a fluidic valve 106 comprising a stator groove 164. The sample management device 100 according to FIG. 17 corresponds to a pull configuration.

Figure 18:
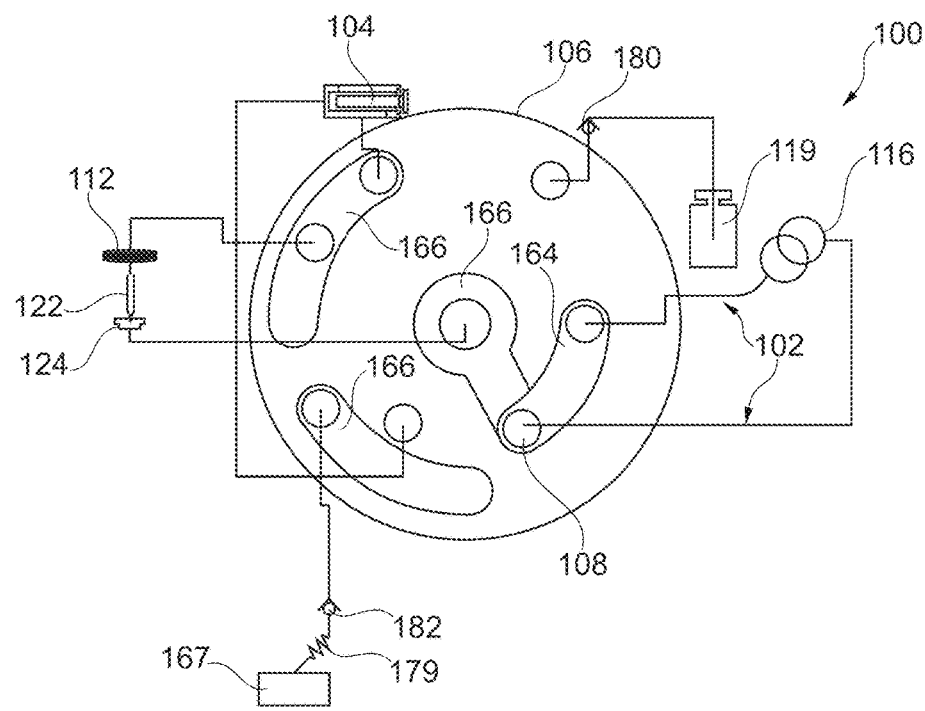
FIG. 18 illustrates a sample management device according to another exemplary embodiment of the invention.

According to FIG. 18, a sample management device 100 for preparation applications is shown which has a fluidic valve 106 comprising a stator groove 164. The sample management device 100 according to FIG. 18 corresponds to a push sample configuration.

Figure 19:
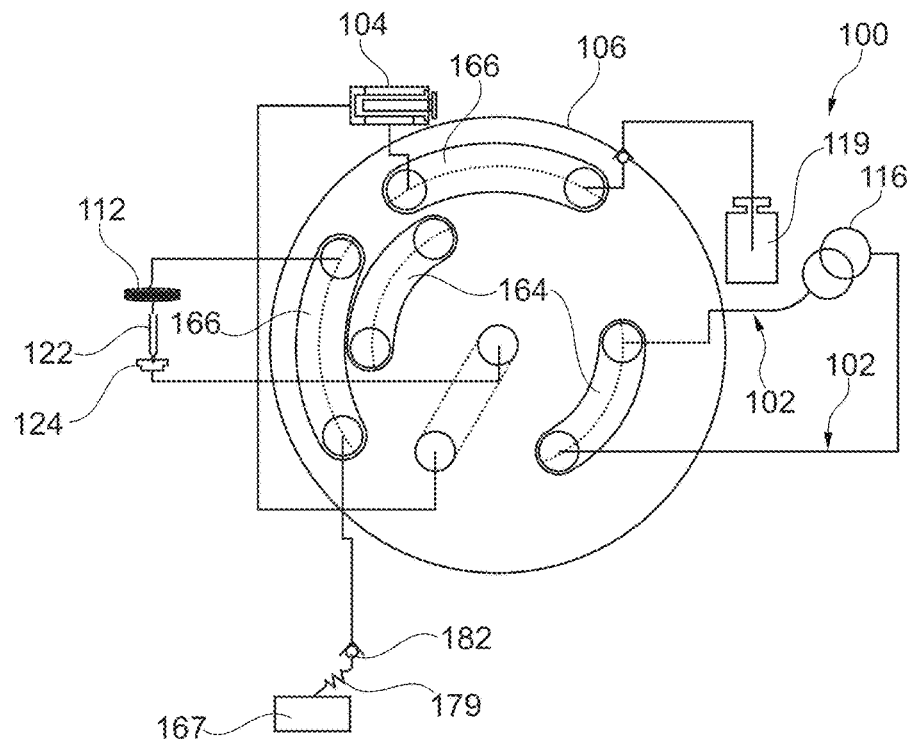
FIG. 19 illustrates a sample management device according to another exemplary embodiment of the invention.

According to FIG. 19, a sample management device 100 corresponding to a push sample configuration is illustrated.

Figure 20:
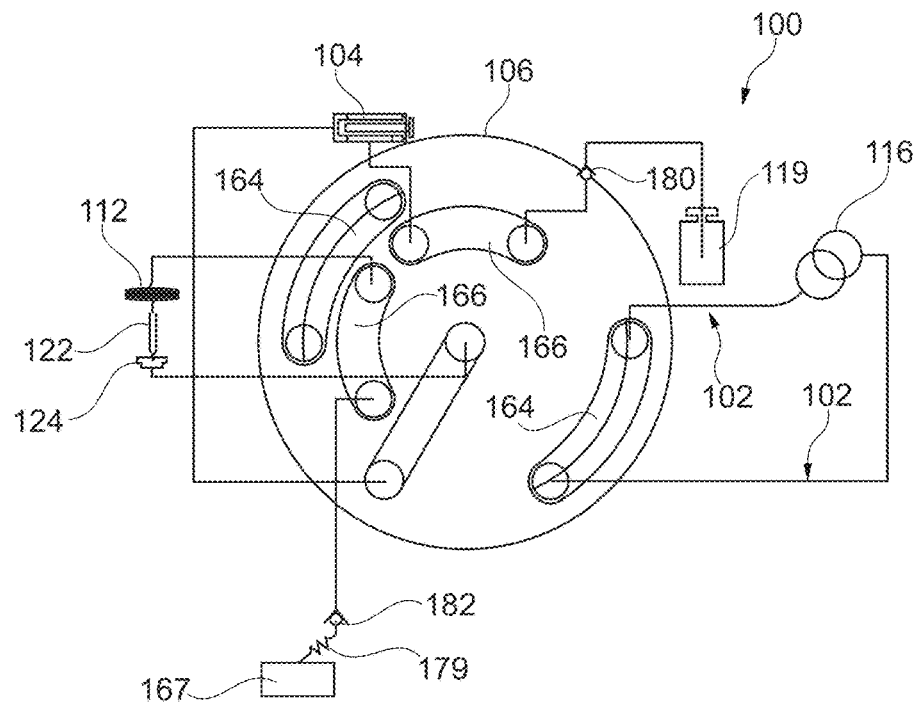
FIG. 20 illustrates a sample management device according to another exemplary embodiment of the invention.

According to FIG. 20, another sample management device 100 corresponding to a sample push configuration is illustrated.

Figure 21:
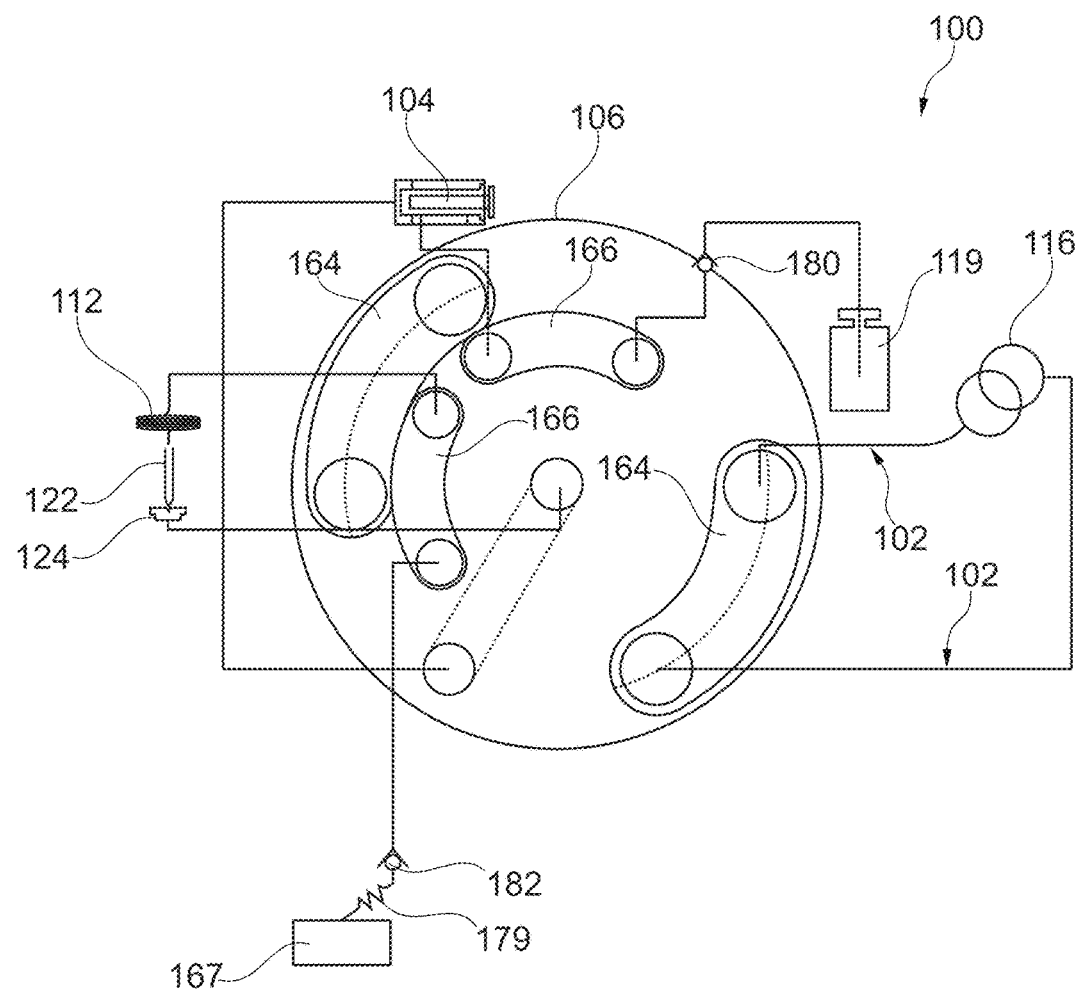
FIG. 21 illustrates a sample management device according to another exemplary embodiment of the invention.

According to FIG. 21, a sample management device 100 corresponding to a pre-push configuration is illustrated.

It should be noted that the term "comprising" does not exclude other elements or features and the term "a" or "an" does not exclude a plurality. Also elements described in association with different embodiments may be combined. It should also be noted that reference signs in the claims shall not be construed as limiting the scope of the claims.

The invention claimed is:
1. A sample management device, comprising:
a source flow path in which a fluidic sample can flow;
a volume flow adjustment pump configured to adjust a volume flow of the fluidic sample to be branched off from the source flow path at a fluidic coupling point; and
a fluidic valve fluidically coupled with the source flow path and with the volume flow adjustment pump;
wherein the fluidic valve is switchable into a branch off state in which the fluidic coupling point is established within the source flow path to branch off an adjustable volume of the fluidic sample from the source flow path via the fluidic coupling point while a flow of the fluidic sample in the source flow path continues, wherein:
the fluidic valve is configured so that, in the branch off state, the volume flow adjustment pump is fluidically coupled with the source flow path via the fluidic coupling point,
the fluidic coupling point has at least three fluid connections, and
the fluidic coupling point is located in an interior of the fluidic valve.

2. The sample management device according to claim 1, comprising at least one of the following features:
wherein, in the branch off state, two of the at least three fluid connections at the fluidic coupling point are fluidically coupled to or form part of the source flow path and another one of the at least three fluid connections is fluidically coupled to the volume flow adjustment pump;
wherein the at least three fluid connections comprise two fluidic conduits of the fluidic valve fluidically coupled with one another in the branch off state.

3. The sample management device according to claim 1, wherein the volume flow adjustment pump is configured to adjust the volume flow of the fluidic sample to be branched off from the source flow path.

4. The sample management device according to claim 1, comprising a destination flow path fluidically coupled with the fluidic valve, wherein the fluidic valve is switchable into a sample supply state in which the branched off fluidic sample is supplied into the destination flow path.

5. The sample management device according to claim 1, wherein the source flow path comprises a sample separation apparatus for separating the fluidic sample in fractions.

6. The sample management device according to claim 5, comprising a destination flow path fluidically coupled with the fluidic valve, wherein the fluidic valve is switchable into a sample supply state in which the branched off fluidic sample is supplied into the destination flow path, and the destination flow path comprises a further sample separation apparatus for further separating the fractions into subfractions.

7. The sample management device according to claim 1, comprising a needle, a seat and an accommodation volume between the volume flow adjustment pump and the fluidic valve, wherein the needle is drivable selectively into the seat or out of the seat for transferring a substance between the accommodation volume and an external entity.

8. The sample management device according to claim 7, comprising a sample separation apparatus into which the branched off fluidic sample is injectable from the external entity.

9. The sample management device according to claim 8, wherein the sample separation apparatus comprises a further needle, a further seat and a further accommodation volume, wherein the further needle is drivable selectively into the further seat or out of the further seat for transferring the branched off fluidic sample from the external entity into the further accommodation volume.

10. The sample management device according to claim 1, wherein the fluidic valve is switchable in a pressure adjustment state in which the source flow path is fluidically decoupled from the volume flow adjustment pump and in which the volume flow adjustment pump is operable for adjusting a pressure between the volume flow adjustment pump and the fluidic valve.

11. The sample management device according to claim 10, wherein the volume flow adjustment pump is operable for adjusting the pressure in the pressure adjustment state to reduce a pressure difference with regard to another pressure in the source flow path prior to switching the fluidic valve in the branch off state.

12. The sample management device according to claim 1, wherein the fluidic valve has:
a source flow-in port through which the fluidic sample can be guided to flow from the source flow path into the fluidic valve;
a source flow-out port through which branched off fluidic sample can flow away from the source flow path and not-branched off fluidic sample can remain flowing within the source flow path;
a branch off port through which the branched off fluidic sample can flow to a sample accommodation volume in fluid communication with the volume flow adjustment pump.

13. The sample management device according to claim 12, wherein, in the branch off state, the source flow-out port is equal to the fluidic coupling point.

14. The sample management device according to claim 1, comprising at least one of the following features:
wherein the fluidic valve is switchable into at least one other state in which the volume flow adjustment unit and the source flow path are fluidically decoupled from one another;
wherein the source flow path has a flow-in port through which the fluidic sample flows into the source flow path and has a flow-out port through which the fluidic sample flows out of the source flow path;
wherein the fluidic valve is switchable into at least one other state in which no fluidic coupling point fluidically coupling the volume flow adjustment pump and the source flow path is established within the source flow path;
wherein the fluidic coupling point is defined by a fluidic coupling position between the source flow path and a channel end point of a volume flow adjustment path including the volume flow adjustment pump;
the sample management device is configured so that a flow of the fluidic sample in the source flow path continues substantially undisturbed in the branch off state;
the sample management device is configured so that a flow of the fluidic sample in the source flow path continues uninterruptedly in the branch off state;
wherein the fluidic coupling point corresponds to a fluid port;
wherein the volume flow adjustment pump comprises a predefined fluidic restriction;
wherein the source flow path is configured for closed-loop fluid processing;
wherein the source flow path comprises a fluid reactor for subjecting the fluidic sample to a reaction;
wherein the volume flow adjustment pump is operable so that the volume of the fluidic sample to be branched off from the source flow path flows via the fluidic coupling point into a sample accommodation volume.

15. A sample separation system for separating a fluidic sample, wherein the sample separation system comprises:
a fluid drive configured to drive a mobile phase;
a separation unit configured to separate the fluidic sample in the mobile phase;
a sample management device according to claim 1 for branching off an adjusted volume of the fluidic sample for injection between the fluid drive and the separation unit.

16. The sample separation system of claim 15, further comprising at least one of the following features:
- a detector configured to detect separated fractions of the fluidic sample;
- a fractioner unit configured to collect separated fractions of the fluidic sample;
- a degassing apparatus for degassing the mobile phase;
- the sample separation system is configured as a chromatography sample separation system.

17. A method of managing a fluidic sample, the method comprising:
- providing a fluidic sample flowing in a source flow path;
- fluidically coupling a fluidic valve with the source flow path and with a volume flow adjustment pump configured to adjust a volume flow of the fluidic sample to be branched off from the source flow path at a fluidic coupling point;
- switching the fluidic valve into a branch off state in which the fluidic coupling point is established within the source flow path; and
- branching off a volume, being adjusted by the volume flow adjustment pump, of the fluidic sample from the source flow path via the fluidic coupling point while a flow of the fluidic sample in the source flow path continues and while the fluidic valve is in the branch off state, wherein:
- the fluidic valve is configured so that, in the branch off state, the volume flow adjustment pump is fluidically coupled with the source flow path via the fluidic coupling point,
- the fluidic coupling point has at least three fluid connections, and
- the fluidic coupling point is located in an interior of the fluidic valve.

* * * * *